(12) United States Patent
Shin et al.

(10) Patent No.: US 9,201,061 B2
(45) Date of Patent: Dec. 1, 2015

(54) KRT19 STABILIZING HER2 AND USE THEREOF

(71) Applicant: Industry-University Cooperation Foundation Hanyang University, Seoul (KR)

(72) Inventors: In-Cheol Shin, Seoul (KR); Tae-Hoon Lee, Gyeongbuk (KR); Ji-Hyun Ju, Seoul (KR); Kyung-Min Lee, Seoul (KR); Won-Seok Yang, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 13/777,501

(22) Filed: Feb. 26, 2013

(65) Prior Publication Data

US 2014/0242069 A1   Aug. 28, 2014

(51) Int. Cl.
| | |
|---|---|
| *A61K 31/70* | (2006.01) |
| *A61K 39/395* | (2006.01) |
| *G01N 33/50* | (2006.01) |
| *A61K 31/713* | (2006.01) |
| *C12N 15/113* | (2010.01) |
| *C07K 16/18* | (2006.01) |
| *C12Q 1/68* | (2006.01) |
| *A61K 39/00* | (2006.01) |

(52) U.S. Cl.
CPC .......... *G01N 33/5011* (2013.01); *A61K 31/713* (2013.01); *C07K 16/18* (2013.01); *C12N 15/1135* (2013.01); *A61K 2039/505* (2013.01); *C12N 2310/11* (2013.01); *C12N 2310/14* (2013.01); *C12N 2310/16* (2013.01); *G01N 2333/4742* (2013.01); *G01N 2333/485* (2013.01)

(58) Field of Classification Search
None
See application file for complete search history.

(56) References Cited

PUBLICATIONS

Luqmani et al. International Journal of Oncology vol. 34:23242, 2009.*

* cited by examiner

*Primary Examiner* — Sean McGarry
(74) *Attorney, Agent, or Firm* — Ann Wieczorek; Mayer & Williams PC

(57) ABSTRACT

Provided is a method of decreasing the stability of HER2 (human epidermal growth factor receptor 2) in a cell or individual comprising administering an effective amount of an expression or activity inhibitor of KRT19 (cytokeratin 19) to the cell or individual.

11 Claims, 30 Drawing Sheets

KRT19

MCF-7 vec      MCF-7 HER2

■ Normal filamentous shape
☐ Granulous shape

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: HER2 Fwd primer

```
<400> SEQUENCE: 1
aactgcaccc actcctgtgt                                              20

<210> SEQ ID NO 2
<211> LENGTH: 20
<212> TYPE: DNA
<213> ORGANISM: Artificial Sequence
<220> FEATURE:
<223> OTHER INFORMATION: HER2 Rev primer

<400> SEQUENCE: 2
tgatgaggat cccaaagacc                                              20

<210> SEQ ID NO 3
<211> LENGTH: 23
<212> TYPE: DNA
<213> ORGANISM: Artificial Sequence
<220> FEATURE:
<223> OTHER INFORMATION: human KRT19 Fwd primer

<400> SEQUENCE: 3
gcactacagc cactactaca cga                                          23

<210> SEQ ID NO 4
<211> LENGTH: 19
<212> TYPE: DNA
<213> ORGANISM: Artificial Sequence
<220> FEATURE:
<223> OTHER INFORMATION: human KRT19 Rev primer

<400> SEQUENCE: 4
ctcatgcgca gagcctgtt                                               19

<210> SEQ ID NO 5
<211> LENGTH: 20
<212> TYPE: DNA
<213> ORGANISM: Artificial Sequence
<220> FEATURE:
<223> OTHER INFORMATION: mouse KRT19 Fwd primer

<400> SEQUENCE: 5
tgctgaagcc acctaccttg                                              20

<210> SEQ ID NO 6
<211> LENGTH: 20
<212> TYPE: DNA
<213> ORGANISM: Artificial Sequence
<220> FEATURE:
<223> OTHER INFORMATION: mouse KRT19 Rev primer

<400> SEQUENCE: 6
atactcctgg ttctggcgct                                              20

<210> SEQ ID NO 7
<211> LENGTH: 21
<212> TYPE: DNA
<213> ORGANISM: Artificial Sequence
<220> FEATURE:
<223> OTHER INFORMATION: human Actin Fwd primer

<400> SEQUENCE: 7
gctcgtcgtc gacaacggct c                                            21
```

```
<210> SEQ ID NO 8
<211> LENGTH: 25
<212> TYPE: DNA
<213> ORGANISM: Artificial Sequence
<220> FEATURE:
<223> OTHER INFORMATION: human Actin Rev primer

<400> SEQUENCE: 8
caaacatgat ctgggtcatc ttctc                                             25

<210> SEQ ID NO 9
<211> LENGTH: 24
<212> TYPE: DNA
<213> ORGANISM: Artificial Sequence
<220> FEATURE:
<223> OTHER INFORMATION: mouse Actin Fwd primer

<400> SEQUENCE: 9
ttctttgcag ctccttcgtt gccg                                              24

<210> SEQ ID NO 10
<211> LENGTH: 24
<212> TYPE: DNA
<213> ORGANISM: Artificial Sequence
<220> FEATURE:
<223> OTHER INFORMATION: mouse Actin Rev primer

<400> SEQUENCE: 10
tggatggcta cgtacatggc tggg                                              24

<210> SEQ ID NO 11
<211> LENGTH: 167
<212> TYPE: PRT
<213> ORGANISM: Artificial Sequence
<220> FEATURE:
<223> OTHER INFORMATION: KRT19 epitope sequence (7~173)

<400> SEQUENCE: 11

Arg Gln Ser Ser Ala Thr Ser Ser Phe Gly Gly Leu Gly Gly Gly Ser
  1               5                  10                  15

Val Arg Phe Gly Pro Gly Val Ala Phe Arg Ala Pro Ser Ile His Gly
             20                  25                  30

Gly Ser Gly Gly Arg Gly Val Ser Val Ser Ser Ala Arg Phe Val Ser
         35                  40                  45

Ser Ser Ser Ser Gly Ala Tyr Gly Gly Gly Tyr Gly Val Leu Thr
     50                  55                  60

Ala Ser Asp Gly Leu Leu Ala Gly Asn Glu Lys Leu Thr Met Gln Asn
 65                  70                  75                  80

Leu Asn Asp Arg Leu Ala Ser Tyr Leu Asp Lys Val Arg Ala Leu Glu
                 85                  90                  95

Ala Ala Asn Gly Glu Leu Glu Val Lys Ile Arg Asp Trp Tyr Gln Lys
            100                 105                 110

Gln Gly Pro Gly Pro Ser Arg Asp Tyr Ser His Tyr Tyr Thr Thr Ile
        115                 120                 125

Gln Asp Leu Arg Asp Lys Ile Leu Gly Ala Thr Ile Glu Asn Ser Arg
    130                 135                 140

Ile Val Leu Gln Ile Asp Asn Ala Arg Leu Ala Ala Asp Asp Phe Arg
145                 150                 155                 160

Thr Lys Phe Glu Thr Glu Gln
                165
```

```
<210> SEQ ID NO 12
<211> LENGTH: 253
<212> TYPE: PRT
<213> ORGANISM: Artificial Sequence
<220> FEATURE:
<223> OTHER INFORMATION: KRT19 epitope sequence (78~330)

<400> SEQUENCE: 12

Gly Asn Glu Lys Leu Thr Met Gln Asn Leu Asn Asp Arg Leu Ala Ser
  1               5                  10                  15

Tyr Leu Asp Lys Val Arg Ala Leu Glu Ala Ala Asn Gly Glu Leu Glu
             20                  25                  30

Val Lys Ile Arg Asp Trp Tyr Gln Lys Gln Gly Pro Gly Pro Ser Arg
         35                  40                  45

Asp Tyr Ser His Tyr Tyr Thr Thr Ile Gln Asp Leu Arg Asp Lys Ile
     50                  55                  60

Leu Gly Ala Thr Ile Glu Asn Ser Arg Ile Val Leu Gln Ile Asp Asn
 65                  70                  75                  80

Ala Arg Leu Ala Ala Asp Asp Phe Arg Thr Lys Phe Glu Thr Glu Gln
                 85                  90                  95

Ala Leu Arg Met Ser Val Glu Ala Asp Ile Asn Gly Leu Arg Arg Val
            100                 105                 110

Leu Asp Glu Leu Thr Leu Ala Arg Thr Asp Leu Glu Met Gln Ile Glu
        115                 120                 125

Gly Leu Lys Glu Glu Leu Ala Tyr Leu Lys Lys Asn His Glu Glu Glu
    130                 135                 140

Ile Ser Thr Leu Arg Gly Gln Val Gly Gly Gln Val Ser Val Glu Val
145                 150                 155                 160

Asp Ser Ala Pro Gly Thr Asp Leu Ala Lys Ile Leu Ser Asp Met Arg
                165                 170                 175

Ser Gln Tyr Glu Val Met Ala Glu Gln Asn Arg Lys Asp Ala Glu Ala
            180                 185                 190

Trp Phe Thr Ser Arg Thr Glu Glu Leu Asn Arg Glu Val Ala Gly His
        195                 200                 205

Thr Glu Gln Leu Gln Met Ser Arg Ser Glu Val Thr Asp Leu Arg Arg
    210                 215                 220

Thr Leu Gln Gly Leu Glu Ile Glu Leu Gln Ser Gln Leu Ser Met Lys
225                 230                 235                 240

Ala Ala Leu Glu Asp Thr Leu Ala Glu Thr Glu Ala Arg
                245                 250

<210> SEQ ID NO 13
<211> LENGTH: 150
<212> TYPE: PRT
<213> ORGANISM: Artificial Sequence
<220> FEATURE:
<223> OTHER INFORMATION: KRT19 epitope sequence (1~150)

<400> SEQUENCE: 13

Met Thr Ser Tyr Ser Tyr Arg Gln Ser Ser Ala Thr Ser Ser Phe Gly
  1               5                  10                  15

Gly Leu Gly Gly Gly Ser Val Arg Phe Gly Pro Gly Val Ala Phe Arg
             20                  25                  30

Ala Pro Ser Ile His Gly Gly Ser Gly Gly Arg Gly Val Ser Val Ser
         35                  40                  45

Ser Ala Arg Phe Val Ser Ser Ser Ser Gly Ala Tyr Gly Gly Gly
     50                  55                  60
```

-continued

Tyr Gly Gly Val Leu Thr Ala Ser Asp Gly Leu Leu Ala Gly Asn Glu
 65                  70                  75                  80

Lys Leu Thr Met Gln Asn Leu Asn Asp Arg Leu Ala Ser Tyr Leu Asp
                 85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Ser Arg Asp Tyr Ser
        115                 120                 125

His Tyr Tyr Thr Thr Ile Gln Asp Leu Arg Asp Lys Ile Leu Gly Ala
    130                 135                 140

Thr Ile Glu Asn Ser Arg
145                 150

<210> SEQ ID NO 14
<211> LENGTH: 179
<212> TYPE: PRT
<213> ORGANISM: Artificial Sequence
<220> FEATURE:
<223> OTHER INFORMATION: KRT19 epitope sequence (215~393)

<400> SEQUENCE: 14

Lys Lys Asn His Glu Glu Glu Ile Ser Thr Leu Arg Gly Gln Val Gly
 1               5                  10                  15

Gly Gln Val Ser Val Glu Val Asp Ser Ala Pro Gly Thr Asp Leu Ala
             20                  25                  30

Lys Ile Leu Ser Asp Met Arg Ser Gln Tyr Glu Val Met Ala Glu Gln
         35                  40                  45

Asn Arg Lys Asp Ala Glu Ala Trp Phe Thr Ser Arg Thr Glu Glu Leu
     50                  55                  60

Asn Arg Glu Val Ala Gly His Thr Glu Gln Leu Gln Met Ser Arg Ser
 65                  70                  75                  80

Glu Val Thr Asp Leu Arg Arg Thr Leu Gln Gly Leu Glu Ile Glu Leu
                 85                  90                  95

Gln Ser Gln Leu Ser Met Lys Ala Ala Leu Glu Asp Thr Leu Ala Glu
            100                 105                 110

Thr Glu Ala Arg Phe Gly Ala Gln Leu Ala His Ile Gln Ala Leu Ile
        115                 120                 125

Ser Gly Ile Glu Ala Gln Leu Gly Asp Val Arg Ala Asp Ser Glu Arg
    130                 135                 140

Gln Asn Gln Glu Tyr Gln Arg Leu Met Asp Ile Lys Ser Arg Leu Glu
145                 150                 155                 160

Gln Glu Ile Ala Thr Tyr Arg Ser Leu Leu Glu Gly Gln Glu Asp His
                165                 170                 175

Tyr Asn Asn

<210> SEQ ID NO 15
<211> LENGTH: 400
<212> TYPE: PRT
<213> ORGANISM: Homo sapiens

<400> SEQUENCE: 15

Met Thr Ser Tyr Ser Tyr Arg Gln Ser Ser Ala Thr Ser Ser Phe Gly
 1               5                  10                  15

Gly Leu Gly Gly Gly Ser Val Arg Phe Gly Pro Gly Val Ala Phe Arg
             20                  25                  30

Ala Pro Ser Ile His Gly Gly Ser Gly Gly Arg Gly Val Ser Val Ser
         35                  40                  45

```
Ser Ala Arg Phe Val Ser Ser Ser Ser Gly Ala Tyr Gly Gly Gly
    50                  55                  60
Tyr Gly Gly Val Leu Thr Ala Ser Asp Gly Leu Leu Ala Gly Asn Glu
 65                  70                  75                  80
Lys Leu Thr Met Gln Asn Leu Asn Asp Arg Leu Ala Ser Tyr Leu Asp
                 85                  90                  95
Lys Val Arg Ala Leu Glu Ala Ala Asn Gly Glu Leu Glu Val Lys Ile
                100                 105                 110
Arg Asp Trp Tyr Gln Lys Gln Gly Pro Gly Pro Ser Arg Asp Tyr Ser
            115                 120                 125
His Tyr Tyr Thr Thr Ile Gln Asp Leu Arg Asp Lys Ile Leu Gly Ala
    130                 135                 140
Thr Ile Glu Asn Ser Arg Ile Val Leu Gln Ile Asp Asn Ala Arg Leu
145                 150                 155                 160
Ala Ala Asp Asp Phe Arg Thr Lys Phe Glu Thr Glu Gln Ala Leu Arg
                165                 170                 175
Met Ser Val Glu Ala Asp Ile Asn Gly Leu Arg Arg Val Leu Asp Glu
                180                 185                 190
Leu Thr Leu Ala Arg Thr Asp Leu Glu Met Gln Ile Glu Gly Leu Lys
    195                 200                 205
Glu Glu Leu Ala Tyr Leu Lys Lys Asn His Glu Glu Glu Ile Ser Thr
210                 215                 220
Leu Arg Gly Gln Val Gly Gly Gln Val Ser Val Glu Val Asp Ser Ala
225                 230                 235                 240
Pro Gly Thr Asp Leu Ala Lys Ile Leu Ser Asp Met Arg Ser Gln Tyr
                245                 250                 255
Glu Val Met Ala Glu Gln Asn Arg Lys Asp Ala Glu Ala Trp Phe Thr
                260                 265                 270
Ser Arg Thr Glu Glu Leu Asn Arg Glu Val Ala Gly His Thr Glu Gln
    275                 280                 285
Leu Gln Met Ser Arg Ser Glu Val Thr Asp Leu Arg Arg Thr Leu Gln
    290                 295                 300
Gly Leu Glu Ile Glu Leu Gln Ser Gln Leu Ser Met Lys Ala Ala Leu
305                 310                 315                 320
Glu Asp Thr Leu Ala Glu Thr Glu Ala Arg Phe Gly Ala Gln Leu Ala
                325                 330                 335
His Ile Gln Ala Leu Ile Ser Gly Ile Glu Ala Gln Leu Gly Asp Val
                340                 345                 350
Arg Ala Asp Ser Glu Arg Gln Asn Gln Glu Tyr Gln Arg Leu Met Asp
            355                 360                 365
Ile Lys Ser Arg Leu Glu Gln Glu Ile Ala Thr Tyr Arg Ser Leu Leu
    370                 375                 380
Glu Gly Gln Glu Asp His Tyr Asn Asn Leu Ser Ala Ser Lys Val Leu
385                 390                 395                 400
```

KRT19 STABILIZING HER2 AND USE THEREOF

BACKGROUND

The present disclosure relates to KRT19 (cytokeratin 19)-HER2/erbB2/neu (human epidermal growth factor receptor 2) interaction and the use thereof, and more particularly, to the development of a method of treating HER2-positive cancer, and an anticancer drug, using the interaction between KRT19 and HER2 and related molecular mechanisms.

HER2 is a member of the epidermal growth factor receptor (EGFR) family, one of important signaling systems that involve in the proliferation and survival of breast cancer cells. The receptor tyrosine kinases of the EGFR family consist of four receptors: erbB1, HER2/erbB2, erbB3 and erbB4, and they are known to involve in the regulation of adhesion, migration and differentiation of cells as well as cell proliferation and survival. Among all four erb family members, HER2/erbB2 does not bind any ligand; however, it is known to be the most potent oncogene in breast cancer.

Whereas in a case that HER2 levels are normal, HER2 involves in the growth and development of normal breast tissue, abnormal overexpression or amplification of HER2 causes the disruption of normal cellular regulation and the formation of aggressive tumor cells in breast tissue. For this process, HER2 is activated by the oligomerization with other members of EGFR family, and the activated HER2 phosphorylates a number of downstream molecules that in turn activate a variety of signaling cascades. Among these, SOS-Ras-Raf-MEK-MAPK signaling pathway involved in cell proliferation and PI3K-Akt signaling pathway inhibiting apoptosis are representative mechanisms for cancer proliferation.

Preclinical and clinical studies showed that HER2 overexpression is an important phenomenon which occurs from early-stage of cancer incidence and plays an important role in the growth and progression of cancer. Overexpression of HER2 occurs in approximately 20-30% of invasive breast cancers and overexpression is known to involve in poor prognosis of breast cancer that is more malignant and aggressive.

There is much interest in HER2 in the breast cancer research because amplification or overexpression of HER2 has value as a prognostic marker and as a predictive factor for response to treatment in breast cancer patients. There is a controversy about the value as a prognostic factor; however, reports that a bad prognosis and significantly short survival time have been observed with amplification of HER2 gene and the consequent overexpression of protein have been presented through many conferences.

Especially, in metastatic or primary breast cancer patients, the amplification or overexpression of HER2 becomes a decisive marker for the treatment of cancer patients using Herceptin, a monoclonal antibody drug. The importance of HER2 was appreciated and in the year 2000, and HER2 was included in tumor markers for breast cancer proposed by ASCO (American Society of Clinical Oncology), and most guidelines for treatment recommended that HER2 test be carried out for all primary breast cancer patients. Accordingly, there is a need for standardized assessment of HER2 in breast cancer tissue.

However, conventional methods of diagnosis and treatment using Herceptin showed low sensitivity and thus exhibited very low efficiency for a low level of HER2. Thus, there was a need for investigation of molecular mechanism involved in the overexpression of HER2, to find a method of detecting only HER2-overexpressing cells effectively and inhibiting their HER2 expression.

Accordingly, as a result of studies to identify the relations of KRT19 expression in the HER2-overexpressing cells and molecular mechanisms thereof, the present inventors found newly that KRT19 is involved in the MEK/ERK pathway and the Atk kinase-mediated phosphorylation on Ser35 and binds to HER2 to contribute to the stability of HER2. Therefore, the present invention has been completed by finding out anticancer effects which can inhibit the stability of HER2 through the inhibition of KRT19 expression.

SUMMARY

The present disclosure provides a method of decreasing the stability of HER2 through the inhibition of KRT19 expression or activity.

The present disclosure also provides an anticancer composition for HER2-positive cancers including an expression or activity inhibitor of KRT19 as an active ingredient.

The present disclosure also provides a method of screening candidate substances for an anticancer drug using the interconnection between KRT19 and HER2 or its related molecular mechanisms.

In accordance with one aspect of the present invention, a method of decreasing the stability of HER2 (human epidermal growth factor receptor 2) in a cell or individual includes: administering an effective amount of an expression or activity inhibitor of KRT19 (cytokeratin 19) to the cell or individual.

The individual may be a patient having a HER2-positive cancer.

The inhibition of KRT19 expression may be carried out using any one selected from the group consisting of antisense oligonucleotide, short interfering RNA, short hairpin RNA, and RNAi, which binds complementarily to mRNA of KRT19 gene. Especially, short hairpin RNA (shRNA) may be preferable.

The inhibition of KRT19 activity may be carried out using any one selected from the group consisting of aptamer, compound, peptide, peptide mimetic, and antibody, which binds specifically to KRT19 protein.

In addition, the method may further include: administering a therapeutically effective amount of an expression or activity inhibitor of HER2. The expression inhibitor of HER2 may be selected from the group consisting of antisense oligonucleotide, short interfering RNA, short hairpin RNA, and RNAi, which binds complementarily to mRNA of HER2 gene, and the activity inhibitor of HER2 may be selected from the group consisting of antibody, aptamer, compound, peptide, and peptide mimetic, which binds specifically to HER2 protein, and the antibody which binds specifically to HER2 protein may be Herceptin.

In accordance with another aspect of the present invention, a method of treating a patient having a HER2-positive cancer includes: administering a therapeutically effective amount of an expression or activity inhibitor of KRT19 (cytokeratin 19) to the cancer patient.

In the treating method, the patient may have resistance to Herceptin.

In the treating method, the expression inhibitor of KRT19 may be selected from the group consisting of antisense oligonucleotide, short interfering RNA, short hairpin RNA, and RNAi, which binds complementarily to mRNA of KRT19 gene, and the activity inhibitor of KRT19 may be selected from the group consisting of antibodies, aptamer, compound, peptide, and peptide mimetic, which bind specifically to KRT19 protein.

In accordance with one embodiment of the treating method of the present invention, the treating method may include:

administering further a therapeutically effective amount of an expression or activity inhibitor of HER2 to the patient. The expression inhibitor of HER2 may be selected from the group consisting of antisense oligonucleotide, short interfering RNA, short hairpin RNA, and RNAi, which binds complementarily to mRNA of HER2 gene, and the activity inhibitor of HER2 may be selected from the group consisting of antibodies, aptamer, compound, peptide, and peptide mimetic, which binds specifically to HER2 protein, and the antibody which binds specifically to HER2 protein may be Herceptin.

Particularly, this combined treating method directly targets both HER2 and KRT19 at the same time, and thus can exhibit more effective anticancer functions, and particularly, can exhibit more efficient anticancer functions for cancers which have resistance to the use of conventional HER2 inhibitors (FIG. 9).

In accordance with yet another aspect of the present invention, a method of screening candidate substances for an anticancer drug includes:

(a) treating a KRT19 and HER2 expressing cell with a candidate substance;

(b) measuring the expression level of KRT19 or HER2, or the binding level between KRT19 and HER2; and (c) selecting the candidate substance which decreases the expression level of KRT19 or HER2, or the binding level between KRT19 and HER2, compared to a control untreated with the candidate.

Particularly, the method may further includes: determining one or more of the following details:

(i) enzymatic activity of MEK/ERK;
(ii) Akt-mediated Ser35 phosphorylation of KRT19; and
(iii) shape of KRT19, and selecting the candidate substance, which decreases the enzymatic activity of MEK/ERK in the case of (i), decreases the Ser35 phosphorylation of KRT19 protein in the case of (ii), or which modifies the shape of KRT19 from a filamentous to a granulous shape in the case of (iii).

In accordance with still another aspect of the present invention, a method of screening candidate substances for an anticancer drug includes:

(a) preparing KRT19 protein, or Ser35-phosphorylated KRT19 protein and HER2 protein;

(b) combining Ser35-phosphorylated KRT19 protein with HER2 protein in the presence of a candidate substance, or combining KRT19 with HER2 protein in the presence of Akt and a candidate substance; and (c) selecting the candidate substance which inhibits the binding between Ser35-phosphorylated KRT19 protein or KRT19 protein and HER2 protein as compared with the absence of the candidate substance.

In the method, the binding between Ser35-phosphorylated KRT19 protein or KRT19 protein and HER2 protein may be determined by a yeast two-hybrid analysis, surface plasmon resonance analysis, co-immunoprecipitation assay, fluorescence resonance energy transfer (FRET) analysis, bimolecular fluorescence complementation (BiFC), protein chip or phage display.

In this way, the present invention can provide overall respects regarding diagnosis of HER2-positive cancers, methods of treating or preventing cancers using inhibitors of KRT19, based on the HER2-KRT19 interaction mechanism.

The present inventors found novel targets which can inhibit the expression of HER2 and the expression or activity of KRT19, thereby inhibiting growth of HER2-positive cancer cells effectively and inducing apoptosis.

In addition, by determining the specific binding between KRT19 and HER2 and selecting substances which inhibit the specific binding between KRT19 and HER2, the present invention can screen substances having an anticancer activity which attenuate the stability of HER2. Accordingly, the present invention can be very useful for the prevention, alleviation, and treatment of HER2-related diseases such as breast cancer.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1A:
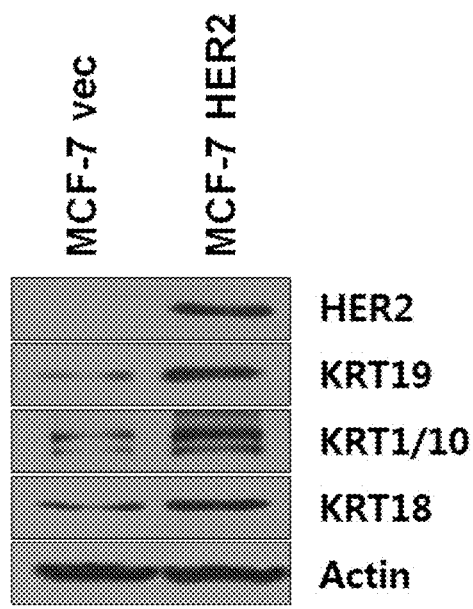
FIGS. 1A and 1B are the results of RT-PCR and Western blot analysis of the expression relation between HER2 and KRT19 in MCR-7 HER2 cell line (FIG. 1A) and other breast cancer cell lines (FIG. 1B)

Technologies and procedures described or referenced herein are generally well understood and commonly employed using conventional methodology by those skilled in the art, such as, for example, the widely utilized molecular cloning methodologies described in Sambrook et al., *Molecular Cloning*: A Laboratory Manual 2nd. Edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Before describing methods and analyses of the present invention, it is to be understood that the present invention is not limited to particular methodologies, protocols, cell lines, animal species or genera, constructs, and reagents described, as such may, of course, vary.

Definition of the terms used in the present invention is as follows.

"Subject" or "patient" refers to any single individual in need of treatment, including humans, cows, dogs, guinea pigs, rabbits, chicken, insects, etc. In addition, any subject, who does not exhibit any clinical findings of diseases and participated in clinical trials, or subjects who participated in epidemiological research, or subjects who were used as a control are included in the subject. The subject of one embodiment of the present invention was humans.

"Tissue or cell sample" refers to a similar complex cellular aggregates obtained from a tissue of a subject or patient. A source of the tissue or cell sample may be a fresh, frozen and/or conserved organ or tissue sample; or a solid tissue from biopsy or aspirate; blood or any constituents of blood; a cell of any point of pregnancy or development of a subject. The tissue sample may also be a primary or cultured cell, or cell line.

Optionally, the tissue or cell sample is obtained from primary or metastatic tumor. The tissue sample may include compounds which are not intermixed with the tissue in nature such as preservatives, anticoagulants, buffers, fixatives, nutrients, antibiotics, or the like. For the purposes of the present invention, a "section" of the tissue sample refers to a single part or piece of the tissue sample, e.g. a thin slice of tissue or cells cut from the tissue sample. It is understood that multiple sections of tissue samples may be taken and subjected to analysis according to the present invention, provided that it is understood that the present invention includes a methodology whereby the same section of tissue sample is analyzed at both morphological and molecular levels, or is analyzed with respect to both protein and nucleic acid.

"Nucleic acid" refers to any DNA or RNA, for example, chromosomal, mitochondrial, viral and/or bacterial nucleic acid present in tissue sample. "Nucleic acid" encompasses either or both strands of a double stranded nucleic acid molecule and includes any fragment or portion of an intact nucleic acid molecule.

"Gene" refers to any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique sequences adjacent to the gene.

"Primer" refers to oligonucleotide sequences that hybridize to a target complementary RNA or DNA polynucleotide and serve as the starting points for the stepwise synthesis of a polynucleotide from mononucleotides by the action of a nucleotidyltransferase, as occurs for example in a polymerase chain reaction.

"Antibody" is used in the broadest sense, and specifically includes intact monoclonal antibodies, polyclonal antibodies, multi-specific antibodies (for example, bispecific antibodies) formed from at least two intact antibodies, and antibody fragments having biological activity of interest.

"Label" refers to a compound or composition which is conjugated or fused directly or indirectly to a reagent such as a nucleic acid probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

"RNAi" refers to RNA interference. RNA interference is a phenomenon of specific gene silencing, which is well conserved in most organisms. It is considered to be a kind of gene surveillance mechanism that cells use to defend against viral infection or inhibit transposons or remove abnormal mRNA. Particularly, a phenomenon of gene silencing by small RNA is referred to as RNA interference in a broad sense, and RNA interference in a narrow sense refers to a phenomenon of mRNA degradation by siRNA. In addition, RNA interference refers to a gene silencing experiment technique using siRNA. "small RNA" refers to a ribonucleic acid of 17-25 nucleotides in length functioning to regulate gene expression in vivo. Small RNA is classified largely into microRNA (shorted to miRNA) and small interfering RNA (shortened to siRNA) depending on its generating mode. miRNA is generated from a partially double stranded RNA (hairpin RNA) and siRNA is derived from long double stranded RNA (dsRNA). To define generally, small RNA which plays an important role in various regulation processes in a living body is a microRNA, and small RNA which is used to experimental technologically regulate the expression of a specific gene is an siRNA. miRNA is produced naturally within cells and binds specifically to a specific mRNA and inhibits protein synthesis from mRNA. siRNA is a small RNA to be introduced artificially into cells and plays a role in binding to a specific mRNA having a complementary sequence and degrading the mRNA.

The term "siRNA" refers to a double stranded DNA molecule which prevents the translation of a target mRNA. A standard technique of introducing siRNA into a cell, including DNA as a template from RNA is transcribed is used. The siRNA may be either dsRNA or shRNA. "dsRNA" refers to a two RNA molecules construct consisting of a single strand and other strand having a complementary sequence to the single strand, and two molecules have complementary sequences and thus, combine together to form a double-stranded RNA molecule. Double stranded nucleic acid sequences may include "sense" or "antisense" sequences of RNA selected from protein coding sequences of a target gene sequence, and RNA molecules selected from non-coding regions of the target gene. The term "shRNA" refers to a siRNA having a stem-loop structure, including first and second regions which are complementary each other, i.e., sense and antisense strands. If the degree of complementarity and space of the complementary region are sufficient, bindings of sufficient base pairs between the regions occurs, and first and second regions are connected by the loop region, and the loop region is made through the absence of base pairs between nucleic acids (or nucleic acid analogs). The loop region of the shRNA is a single strand region between sense and antisense strands, and is also referred to as an "intervened single strand."

The term "proliferation" or "growth" of cells means that a cell divides to increase same one, and it generally refers to increase in cell number in a body of a multicellular organism. If cells proliferate (amplify) in number and the cell number reaches to a certain moment, being their characters changed (differentiated) and being their characters controlled at the same time is normal. The increase in cell number in a body and the neogenesis of cytoplasm in a cell are often identified as growth. However, from a biological point of view of increase in cell number, it is reasonable to consider the period when differentiation does not occur during developmental stage of a multicellular organism as proliferation or growth. The above two terms are mixed up and used interchangeably in the present invention.

"Apoptosis" is used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function.

"Cancer", "tumor", or "malignant" refer to or describe the physiological condition in mammals that is typically characterized by unregulated cell growth. Examples of cancer include, but are not limited to, carcinoma, lymphoma, leukemia, blastoma, and sarcoma.

"Inhibitor" refers to a substance which inhibits, blocks, or reduces the expression or activity of KRT19. Activation mechanism of an inhibitor is not particularly limited. Examples of inhibitors include organic or inorganic compound, and polymeric compound such as proteins, carbohydrates, lipids, composites of various compounds. For example, 'a KRT19 inhibitor' may include a substance which inhibits, blocks, or reduces the activity of KRT19 protein.

"Aptamer" is a single stranded nucleic acid (DNA, RNA, or modified nucleic acid) or peptide having stable three-dimensional structure in itself and characteristic of capable of binding to its target molecule with high affinity and specificity. Since SELEX (Systematic Evolution of Ligands by EXponential enrichment), the aptamer discovery technology had been developed for the first time (Ellington, A D and Szostak, J W., *Nature,* 346: 818-822, 1990), many aptamers capable of binding to a variety of target molecules such as low molecular weight organic matter, peptide, membrane protein have been discovered continuously. Due to its characteristic of capable of binding to target molecules with its inherent high affinity (typically pM range) and specificity, the aptamer can often stand comparison with monoclonal antibodies, and particularly, have high probability of being an alternative to antibodies to such an extent as to be known as chemical antibodies.

"Carriers" may be pharmaceutically acceptable carriers, excipients, or stabilizers, which are non-toxic to cells or mammals exposed thereto at the dosages and concentrations employed. Occasionally, the pharmaceutically acceptable carrier is an aqueous pH buffer solution. Examples of pharmaceutically acceptable carriers include, but are not limited to, buffers, such as phosphate, citrate, and other organic acid buffers; antioxidants such as ascorbic acid; low molecular weight polypeptides (less than about 10 residues); proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween-20, polyethylene glycol (PEG), and Pluronics.

"An effective amount" as used in the present specification refers to a suitable amount influencing beneficial or desirable clinical or biochemical outcomes. The effective amount may be administered one or more times. For the purposes of the present invention, the effective amount of an inhibitor composition is a suitable amount to temporarily palliate, ameliorate, stabilize, restore, slow down or delay the progression of disease state. If a recipient animal can stand administration of the composition or administration of the composition is suitable to the animal, the composition is "pharmaceutically or physiologically acceptable." If the amount administered is physiologically important, the inhibitor composition may be said to be administered in a "therapeutically effective amount." If the presence of the formulation caused a physiologically detectable change in a recipient patient, the formulation is physiologically significant.

"Treatment" refers to an approach to obtain beneficial or desirable clinical outcomes. For the purposes of the present invention, beneficial or desirable outcomes include, but are not limited to, alleviation of symptoms, diminishment of extent of disease, stabilized (i.e., not worsening) state of disease, delay or slowing of disease progression, amelioration or temporary palliation of the disease state, and remission (whether partial or total), whether detectable or undetectable. In addition, "treatment" can mean prolonging survival as compared to expected survival if not receiving treatment. "Treatment" refers to both therapeutic treatment and preventive or prophylactic measures. The treatments include treatments required for already occurred disorders as well as disorders to be prevented. "Palliating" diseases mean diminishing extent of disease state and/or undesirable clinical symptoms and/or slowing down or extending time course of progression as compared to the untreated case.

"About" means an amount, level, value, number, frequency, percent, dimension, size, weight or length changed by 30, 25, 20, 25, 10, 9, 8, 7, 6, 5, 4, 3, 2 or 1% from a reference amount, level, value, number, frequency, percent, dimension, size, weight or length.

Unless otherwise required, through the present disclosure, "has", "have", "comprise(s)", "include(s)", "having", "comprising" and "including" include a suggested step or element, or a group of steps or elements, but it should be understood not to exclude any other step or element, or group of steps or elements.

Herein after, the present invention is described in detail.

The present inventors analyzed the expression level of KRT19 in HER2-expressing tissues, and found that KRT19 were noticeably overexpressed in the HER2-expressing tissues compared to the surrounding non-tumor liver tissue.

HER2 gene encodes a transmembrane glycoprotein of 185,000 daltons in molecular weight belonging to erbB family of epithelial growth factor receptors. Ligand binding induces the formation of erbB-homodimers and erbB-heterodimers leading to activation of cytoplasmic kinase region. HER2 is a receptor having no ligand, and a preferred partner of heterodimerization among ligand-binding EGFR family, EGFR/erbB1, HER3/erbB3 and HER4/erbB4. As a co-receptor, HER2 mediates signal transduction and leads to mitogenesis, apoptosis, angiogenesis, and cell differentiation. Application of any changes to a strictly controlled erbB receptor which signalizes pathways causes to significant abnormalities and tumor formation. HER2 gene is amplified and overexpressed in about 20-30% of invasive breast carcinomas and is related to increased metastatic, latent, and poor prognosis. In addition, the overexpression of HER2 receptor occurs in a variety of human cancers including uterus, prostate, stomach, lung, bladder, and kidney carcinomas.

KRT is a non-aqueous, intracellular fibrous protein present within all cells, and is divided into about 20 types depending on its molecular weight. Among these, KRT19 is present specifically in intestinal mucosal cells, and is widely used with immunohistochemistry staining to diagnose intestinal epithelial oriented tumors.

Particularly, the above KRT19 is known to be overexpressed in breast cancer cells, however, specific molecular mechanism involved in HER2 expression has been not known until now.

The present inventors identified the mechanism by which the stability of HER2 is regulated by the expression of KRT19, and in this connection, identified specifically that (i) the transcriptional activity of KRT19 is regulated through HER2 and MEK/ERK signaling pathway, (ii) KRT19 is relocalized in a cell membrane by Akt-mediated Ser 35 phosphorylation, and is bound to HER2 to stabilize HER2, and (iii) upon Ser35 phosphorylation, the shape of KRT19 is changed from a filamentous to a granulous shape.

This was a new discovery about the molecular mechanism of KRT19-HER2 interaction, and using this, the present inventors paid attention to anticancerous uses through the inhibition of the expression or activity of KRT19 against HER2-positive cancers.

Particularly, conventional Herceptin is an antibody which binds directly to HER2 and thus inhibits the activity of HER2 to exert its anticancer effect, whereas KRT19 of the present invention itself is not a HER2 antibody. KRT19 of the present invention is a protein affecting the activity of HER2 dependent on the complementary interaction between KRT19 and HER2, and features of the present invention inhibit the expression or activity of the above KRT19 (for example, RNAi which is specific to KRT19 or antibodies which are specific to KRT19), thereby exhibiting an anticancer effect through the mechanism which inhibits the expression or activity of the related HER2. That is, novel therapeutic candidates which can inhibit the expression or activity of HER2 were identified.

Accordingly, in the treatment of HER2 positive cancers, the present invention can exhibit more effective anticancer function by using conventional direct inhibitors of HER2 together. Particularly in the case that there is a resistance to conventional HER2 inhibitors, the present invention can inhibit the expression or activity of HER2 through the inhibition of KRT19, and thus, the present invention has greater applicability.

In accordance with one aspect of the present invention, based on this discovery, a method of decreasing the stability of HER2 (human epidermal growth factor receptor 2) in a cell or individual, including administering an effective amount of an expression or activity inhibitor of KRT19 (cytokeratin19) to the cell or individual is provided.

In the method, it is preferable to use a substance selected from the group consisting of substances inhibiting transcription of KRT19 gene, substances inhibiting translation of transcribed KRT19, or substances inhibiting the function of KRT19 protein, but the present invention is not limited to such.

The substance inhibiting transcription may be, but is not limited to, a protein or compound binding to a transcription regulating factor which binds to an enhancer/promoter, which is known to regulate the transcription of KRT19 gene.

The substance inhibiting translation of the mRNA may be, but is not limited to, a low molecular weight compound, RNA, siRNA or shRNA using an antisense nucleic acid sequence preparation or RNAi technique.

Details will be specifically described below:

RNAi

RNAi means a phenomenon of specific gene silencing, but in the present invention, the term is mixed up and used interchangeably with "RNAi reagent" showing this phenomenon, and the RNAi reagent includes an oligomer or polymer of ribonucleic acid (RNA) or deoxyribonucleic acid (DNA), or an analog thereof, and may include modified ribonucleotide residues. Suitable modifications are known in the art (Uhlmann, *Current Opin. Drug Discovery Dev.*, 3(2): 203-213, 2000; and Uhlmann and Peyman, *Chem. Rev.*, 90(4):543-584, 1990).

RNAi encompasses both single-stranded and double-stranded nucleic acid molecules. Double-stranded nucleic acid molecules may be composed of two separate strands or of one strand including two regions which can form a double-stranded structure and a spacer region between the two regions forming a hairpin loop.

The RNAi includes a sequence complementary to a target gene. Regarding the present invention, the expression "complementary to a target gene" means that the sequence is complementary to RNA which is transcribed from a DNA sequence, including pre-mRNA, mRNA, cRNA, of a target gene. "Target gene" refers to one which includes any DNA sequence to be transcribed to RNA, expressed in a cell, tissue or organism. The expressed sequence does not need to be translated to a protein, and examples include pre-mRNA, regulatory RNA, rRNA, and the like. The sequence complementary to the target gene is generally about 19-23 nucleotides long, but may be longer.

RNA interference (RNAi) of KRT19 is a post-transcriptional gene silencing mechanism where degradation of a corresponding KRT19 mRNA occurs by introducing a double-stranded RNA (dsRNA), which is corresponding to KRT19 gene, into a cell or organism. Since, by the RNAi effect, multiple cell divisions are maintained prior to a comeback of KRT19 gene expression, RNAi is a very strong method of making a knockout or 'knockdown' which is aimed at the RNA level. Examples of RNAi type include siRNA or miRNA (microRNA) or short hairpin RNA (shRNA). In one embodiment of the present invention, KRT19 shRNA was used for the KRT19 knockdown method.

Standard methods in molecular biology are used for RNAi technology in gene silencing. dsRNA, which corresponds to the sequence of a target gene to be inactivated, may be produced by a standard method, for example, a double-stranded simultaneous transcription of template DNA using T7 RNA polymerase. A dsRNA production kit in use for RNAi may include commercially available products (for example, a product made by New England Biolabs, Inc.). Transfection methods of dsRNA or a processed plasmid for producing dsRNA are commonly known in the art.

Antisense Nucleic Acid Sequence

For nucleic acid encoding KRT19, antisense nucleic acid molecules may be used as an inhibitor. 'Antisense nucleic acid' includes nucleic acid sequence complementary to a 'sense nucleic acid' encoding KRT19, for example, complementary to a coding strand of a double-stranded cDNA or complementary to mRNA sequence. Thus, the antisense nucleic acid may form hydrogen bonds with the sense nucleic acid. The antisense nucleic acid may be complementary to the entire KRT19 coding strand or its part (e.g. a coding region). Although the antisense nucleic acid molecule may be complementary to the entire coding region of KRT19 mRNA, antisense oligonucleotide is more preferable for only a part (e.g. a translation initiation portion) of the coding or non-coding region of KRT19 mRNA. Antisense oligonucleotide may be, for example, about 5 to 50 nucleotides long.

Antisense nucleic acid may be constructed by using chemical synthesis and enzyme linked reaction according to well-known methods. For example, it may be very easy to produce antisense nucleic acid using chemical synthesis method such as phosphoramidite chemistry of sulfurizing acetonitrile into tetraethylthiuram disulfide, as described in Vu and Hirschbein, *Tetrahedron Lett.*, 32: 30005-30008, 1991.

Examples of a modified nucleotide in use for production of the antisense nucleic acid may be 5-fluorouracil, 5-bromouracil, 5-chlorouracil, 5-iodouracil, hypoxanthine, xanthine, 4-acetylcytosine, 5-(carboxyhydroxylmethyl)-uracil, 1-methylinosine, 2,2-dimethylguanine, 2-methyladenine, 2-methylguanine, 3-methylcytosine, 5-methylcytosine, N6-adenine, 5-carboxy-methylaminomethyl-2-thiouridine, 3-(3-amino-3-N2-carboxypropyl)uracil, 5'-methoxycarboxymethyluracil, 5-methoxyuracil, 2-methylthio-N6-isopentenyl-adenine, 1-methylguanine, 7-methylguanine, 5-methylaminomethyluracil, 5-methoxyaminomethyl-2-thiouracil, beta-D-mannosylqueosine, 2-thiouracil, 4-thiouracil, 5-methyluracil, uracil-5-oxyacetic acid methylester, uracil-5-oxyacetic acid(v), 2,6-diaminopurine, 5-methyl-2-thiouracil, pseudouracil, queosine, 2-thiocytosine, 5-carboxymethylaminomethyluracil, dihydrouracil, beta-D-galactosylqueosine, inosine, N6-isopentenyladenine, 5-methyl-2-thiouracil, (acp3)w and wybutoxosine. As occasion arises, the antisense nucleic acid may be biologically generated by using expression vectors.

Antibodies

The term "antibody" is used in the broadest sense, and specifically encompasses monoclonal antibodies, polyclonal antibodies, multispecific antibodies (e.g. bispecific antibodies) formed from at least two intact antibodies, and antibody fragments so long as they exhibit the desired biological activity.

The term "monoclonal antibody" refers to an antibody obtained from a population of substantially homogeneous antibodies, i.e., the individual antibodies forming the population are identical except for possible mutations occurring in the production of monoclonal antibodies, or bind to an identical epitope. In contrast to polyclonal antibody preparations which typically include different antibodies directed against different determinants (epitopes), each monoclonal antibody is directed against a single determinant on an antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies may be prepared by the hybridoma method first described by Kohler et al., *Nature*, 256:495 (1975), or may be prepared by recombinant DNA methods. The "monoclonal antibodies" may also be isolated from phage antibody libraries using the techniques described in Clackson et al., *Nature*, 352:624-628 (1991); Marks et al., *J. Mol. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Chimeric antibodies" include "primatized" antibodies, including variable domain antigen-binding sequences derived from a non-human primate (e.g. Old World Monkey, anthropoid, etc.) and human constant region sequences.

"Antibody fragments" include a portion of an intact antibody, preferably including the antigen-binding or variable region thereof. Examples of antibody fragments include Fab, Fab', F(ab')$_2$, and Fv fragments; diabodies; linear antibodies; single-chain antibody molecules (ScFv and the like); and multispecific antibodies formed from antibody fragment(s).

"Intact antibodies" include a light chain constant domain (CL) and heavy chain constant domains, CH1, CH2, and CH3, as well as antigen-binding variable regions. The constant domains may be native sequence constant domains (e.g. human native sequence constant domains) or amino acid sequence variant thereof. Preferably, the intact antibody has one or more effector functions, and includes an oligosaccharide structure attached to one or two heavy chains thereof.

Meanwhile, a "naked antibody" is an antibody that is not conjugated to a heterologous molecule, such as a cytotoxic moiety or radiolabel. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Nucleic acid molecules encoding amino acid sequence variants of anti-KRT19 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of KRT19 antibody.

The term "specific binding to KRT19" means that KRT19 is bound exclusively. That is, the binding of an anti-KRT19 antibody according to the present invention is selective for KRT19. Optionally, affinity measurements may be made using methods known to those skilled in the art including using BIACORE measurements. Other suitable methods of determining specific binding will be familiar to those skilled in the art.

In addition, the anti-KRT19 antibody may be modified so as to increase stability and/or half-life. For example, the half-life of an antibody may be increased by PEGylation of the antibody or antibody fragment (see, for example, Chapman A P, *Adv. Drug. Deliv. Rev.*, 54; 531-545, 2002). The antibody in accordance with the present invention may also be generated as an armed molecule adopting enhancement manipulation techniques. In addition, the whole antibody may be constructed, for example by adding the Fc constant part of human immunoglobulin, or by generating mutated antibodies using techniques such as chain shuffling. The antibody may be generated as an immunoconjugate including an antibody component linked to a diagnostic or therapeutic agent. The above linkage may be made by means recognized by those skilled in the art, including chemical conjugation or genetic fusion.

Peptide Mimetics

It is possible to inhibit an original KRT19 polypeptide from binding to HER2 by mimetics (e.g. peptide or non-peptide pharmaceuticals), target a protein-binding domain of KRT19 polypeptide.

Main residues of a non-hydrolyzed peptide analog may be generated by using β-turn dipeptide core (Nagai et al. *Tetrahedron Lett.* 26:647, 1985), keto-methylene pseudopeptides (Ewenson et al. *J. Med. Chem.*, 29:295, 1986; and Ewenson et al. in Peptides: Structure and Function (Proceedings of the $9^{th}$ American Peptide Symposium) Pierce Chemical Co. Rockland, Ill., 1985), azepine (Huffman et al. in Peptides: Chemistry and Biology, G. R. Marshall ed., ESCOM Publisher: Leiden, Netherlands, 1988), benzodiazepine (Freidinger et al. in Peptides; Chemistry and Biology, G. R. Marshall ed., ESCOM Publisher: Leiden, Netherlands, 1988), β-amino alcohol (Garvey et al., in Peptides: Chemistry and Biology, G. R. Marshell ed., ESCOM Publisher: Leiden, Netherlands, 1988).

Aptamer

"Aptamer" is a single stranded nucleic acid (DNA, RNA, or modified nucleic acid) or peptide having stable three-dimensional structure in itself and characteristic of capable of binding to its target molecule with high affinity and specificity. Since SELEX (Systematic Evolution of Ligands by EXponential enrichment), the aptamer discovery technology had been developed for the first time (Ellington, A D and Szostak, J W., *Nature*, 346: 818-822, 1990), many aptamer capable of binding to a variety of target molecules such as low molecular weight organic matters, peptides, membrane proteins have been discovered continuously. Due to its characteristic of capable of binding to target molecules with its inherent high affinity (typically pM range) and specificity, aptamer can often stand comparison with monoclonal antibodies, and particularly, have high probability of being an alternative to antibodies to such an extent as to be known as chemical antibodies. Therefore, by screening an aptamer molecule which binds specifically to KRT19 and determining whether the aptamer molecule can inhibit the activity of KRT19 or not, the aptamer molecule may be used as an inhibitor of KRT19 activity.

In addition, as mentioned above, the method of the present invention may be carried out by using in combination with direct inhibition of HER2 expression or activity.

The direct inhibition of HER2 expression or activity may be carried out using any one selected from the group consisting of antisense oligonucleotide, short interfering RNA, short hairpin RNA, and RNAi, which binds complementarily to mRNA of HER2 gene; or using any one selected from the group consisting of compound, peptide, peptide mimetic, and antibody, which binds complementarily to HER2 protein.

This combined method directly targets HER2 and KRT19 at the same time, and thus can not only exhibit more effective anticancer functions, but also can exhibit anticancer functions by the KRT19 expression or activity-inhibitory effect of the present invention, for cancers which may have resistance to the use of conventional HER2 inhibitors.

Meanwhile, from another aspect, the present invention provides an anticancer composition including an expression or activity inhibitor of KRT19 as an active ingredient.

As described above, the expression inhibitor of KRT19 may be, but is not limited to, any one selected from the group consisting of antisense oligonucleotide, short interfering RNA, short hairpin RNA, and RNAi, which binds complementarily to mRNA of KRT19 gene.

The activity inhibitor of KRT19 may be, but is not limited to, any one selected from the group consisting of compound, peptide, peptide mimetic, and antibody, which binds complementarily to KRT19 protein.

These expression inhibitors or activity inhibitors or KRT19 can induce effective growth inhibition and apoptosis of cancer cells, and thus, can be used effectively as an active ingredient of anticancer therapeutic agents.

The anticancer composition of the present invention includes 0.0001 to 50% by weight of the active ingredient relative to the total weight of the composition.

In the present invention, the cancer to be treated is a HER2-positive cancer, and for example, the cancer to be treated is selected from the group consisting of ovarian cancer, peritoneal cancer, fallopian tubal cancer, breast cancer, non-small cell lung cancer (NSCLC), squamous cell cancer, prostate cancer and colorectal cancer. Preferably, the cancer is a breast cancer.

The anticancer composition of the present invention may further contain one or more types of other active ingredients showing an identical or similar function in addition to the active ingredient.

The anticancer composition of the present may be prepared further including one or more types of a pharmaceutically acceptable carrier in addition to the active ingredient described above. As the pharmaceutically acceptable carrier, saline solution, sterilized water, Linger's solution, buffer saline, dextrose solution, maltodextrin solution, glycerol, ethanol, liposome, and at least one combination thereof, may be used, and if necessary, other typical additives such as antioxidants, buffer solution, bacteriostatic agents, etc., may be added. Moreover, it may be formulated in the form of an injectable formulation such as aqueous solution, suspension and emulsion, a pill, a capsule, a granule, or a tablet by supplementarily adding diluents, dispersing agents, surfactants, binders and lubricants. And it may be used combining a target-specific antibody or other ligands with the carrier to act specifically upon a target organ. Furthermore, it may be preferably formulized according to each disease or ingredients using a suitable method in the art, for example, a method disclosed in Remington's Pharmaceutical Science (the latest edition), Mack Publishing Company, Easton Pa.

The present invention also provides a method of preventing or treating HER2-positive cancers, including administering a pharmaceutically effective amount of the expression or activity inhibitor of KRT19 to an individual.

The administration method is not particularly limited, and thus it may be a parenteral administration (for example, intravenous, subcutaneous, intraperitoneal, or topical application) or oral administration. Although it is preferable to administer parenterally, more preferable to inject intravenously, the present invention is not limited thereto.

The range of dosage varies according to a patient's body weight, age, sex, health status, diet, administration time, administration method, excretion rate, the severity of disease, etc. The daily dosage for a compound is in the range of about 0.1 to 100 mg/kg, preferably 0.5 to 10 mg/kg. It is preferable to administer the formulation one or more times a day, however, the present invention is not limited thereto.

In accordance with another aspect of the present invention, a method of treating a patient having a HER2-positive cancer including administering a therapeutically effective amount of an expression or activity inhibitor of KRT19(cytokeratin 19) to the cancer patient is provided.

Figure 9:
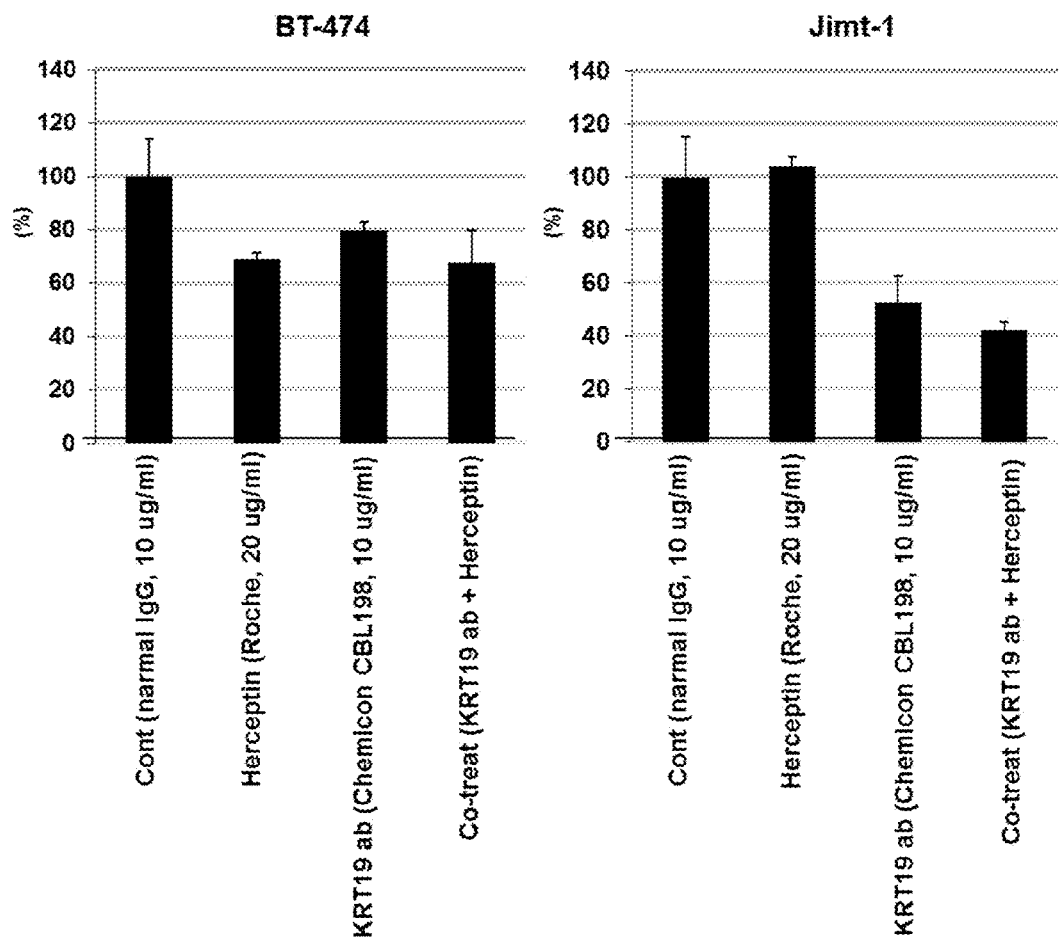
FIG. 9 is the results of a MTT assay using KRT19 antibodies.

In the treating method, the patient may develop a resistance to Herceptin. As proved through embodiments of the present invention, the treating method according to one embodiment of the present invention showed effective cell proliferation-inhibitory and apoptosis-inducing activity on Herceptin-resistant cells which have resistance to Herceptin and thus, difficulties in treating (FIG. 9). Furthermore, when anti-KRT19 antibody was treated, the Herceptin-resistant cell line was changed to be susceptible to Herceptin and thus, the apoptotic ability was more increased in the concomitant treatment with anti-KRT19 antibody and Herceptin than in the single treatment of anti-KRT19 antibody. Therefore, the concomitant treatment with Herceptin may be more promising for patients with Herceptin-resistant cancer.

The expression inhibitor and activity inhibitor of KRT19 and the expression inhibitor and activity inhibitor of HER2 are as described above. In accordance with yet another aspect of the present invention, a method of screening candidate substances for an anticancer drug using a KRT19-dependent expression level of HER2 is provided. In addition, since it is known that substances which not only inhibit the interconnection between KRT19 and HER2 weaken the stability of HER2, and but also have anticancer activity, a method of screening candidate substances for an anticancer drug using a level of the binding between KRT19 and HER2 is provided.

That is, in the present invention, taking into consideration that HER2 is expressed dependently on the expression of KRT19 and HER2 is stabilized by the binding between KRT19 and HER2, it is possible to screen a substance having anticancer activity by selecting the substance that allows the expression of KRT19 or the binding between KRT19 and HER2 to be decreased.

The screening method may be carried out using cells in which KRT19 and HER2 are co-expressed, and may be carried out in a purely cell-free in vitro condition. Since high throughput screening is possible, particularly in the case of the latter, rapid discovery of candidates can be achieved in large quantities.

In particular, the screening method includes:
(a) treating a KRT19 and HER2 expressing cell with a candidate substance;
(b) measuring the expression level of KRT19 or HER2, or the binding level between KRT19 and HER2; and
(c) selecting the candidate substance which decreases the expression level of KRT19 or HER2, or the binding level between KRT19 and HER2, compared to a control untreated with the candidate.

In the screening method, the candidate may be, but is not limited to, any one selected from the group consisting of nucleic acids, proteins, other extracts, and natural products.

In the screening method, the expression level may be determined by measuring the level of transcriptional activity of genes or the amount of expressed proteins, however, the present invention is not limited to such. The level of transcriptional activity may be measured through a luciferase assay and the amount of proteins may be measured through Western blot assay, however, the present invention is not limited to such.

In the screening method, the binding may be measured by an immunoprecipitation method. Immunoprecipitation may be performed by, for example, a method in a document (Harlow and Lane, Antibodies, 511-52, Cold Spring Harbor Laboratory publications, New York, 1988). SDS-PAGE is generally used for analysis of immunoprecipitated proteins, and binding proteins may be analyzed by the molecular weight of proteins using gel of a suitable concentration.

In the screening method, a two-hybrid system, which uses cells, may be employed ("MATCHMAKER Two-Hybrid system", "MATCHMAKER Mammalian Two-Hybrid Assay Kit", "MATCHMAKER one-Hybrid system" (Clontech, Mountain View, Calif.); "HybriZAP Two-Hybrid Vector System" (Stratagene, Santa Clara, Calif.); Reference: Dalton and Treisman, *Cell*, 68: 597-612, 1992; Fields and Sternglanz, *Trends Genet.* 10: 286-92, 1994).

In addition, the screening method may further include determining one or more of the following details:
(i) enzymatic activity of MEK/ERK;
(ii) Akt-mediated Ser35 phosphorylation; and
(iii) shape of KRT19.

The candidate which decreases the enzymatic activity of MEK/ERK in the case of (i), the candidate which decreases the Ser35 phosphorylation in the case of (ii), or the candidate which modifies the shape of KRT19 from a filamentous to a granulous shape in the case of (iii) may be selected as the substance having an anticancer activity.

The above details are based on the molecular mechanism of KRT19-HER2 interaction identified by the present inventors, and specifically, are based on the mechanism that (i) the transcriptional activity of KRT19 is regulated through HER2 and MEK/ERK signaling pathway, (ii) KRT19 is relocalized in a cell membrane by Akt-mediated Ser 35 phosphorylation, and is bound to HER2 to stabilize HER2, and (iii) upon Ser35 phosphorylation, the shape of KRT19 is changed from a filamentous to a granulous shape.

Also, in accordance with still another aspect of the present invention, a method of screening candidate substances for an anticancer drug includes:
(a) preparing KRT19 protein or Ser35-phosphorylated KRT19 protein and HER2 protein;
(b) combining Ser35-phosphorylated KRT19 protein with HER2 protein in the presence of a candidate, or combining KRT19 with HER2 protein in the presence of Akt and a candidate; and
(c) selecting the candidate substance which inhibits the binding between Ser35-phosphorylated KRT19 protein or KRT19 protein and HER2 protein as compared with the absence of the candidate substance.

The method may be carried out by a variety of methods to determine protein-protein interactions, and examples of the determining methods include surface plasmon resonance analysis, co-immunoprecipitation assay, fluorescence resonance energy transfer (FRET) analysis, protein chip, phage display, etc.

Meanwhile, the present invention provides a method of diagnosing HER2-positive cancers, identifying treatment results, or assessing prognosis, the method including measuring the level of KRT19 expression in HER2-positive cancer cells, using one or more of antibodies reactive with KRT19 or nucleic acids complementary to KRT19 gene.

In the method of diagnosing cancers of the present invention, detection of KRT19 expression level higher than a normal range tells that a patient is overexpressing HER2. That is, it means that since there are many HER2-positive cancer cells, the patient is suffering from cancer. In a diagnostic reagent for an individual who has undergone or is undergoing cancer therapy, detection of KRT19 expression level in the normal range tells a success of the cancer therapy, and detection of KRT19 expression level higher than the normal range in the diagnosis reagent tells that the cancer therapy should continue to be applied. Furthermore, in a diagnostic reagent for an individual who is suffering from cancer, detection of normal KRT19 expression level in the normal range tells the prognosis is good; however, detection of KRT19 expression level higher than the normal range in the diagnosis reagent tells that the prognosis is bad.

Expression of a biomarker KRT19 in a sample may be analyzed by a number of methodologies, many of which are known in the art and understood by those skilled in the art, including but not limited to, immunohistochemical and/or Western analysis, quantitative blood based assays (for example, serum ELISA to examine levels of protein expression), biochemical enzymatic activity assays, in situ hybridization, Northern blot analysis and/or PCR analysis of mRNA, and Southern blot analysis or restriction fragment length polymorphism (RFLP) to examine, for example, gene deletion or amplification, as well as any one of the wide variety of assays that can be performed by gene and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis).

In a similar aspect, the present invention provides a kit for diagnosing cancers including one or more of antibodies reactive with KRT19 or nucleic acids complementary to KRT19 gene.

The kit for diagnosing cancers of the present invention may also include one or more substances which are reactive with KRT19, and additionally, a reagent for detecting reaction products and instructions related thereto. For example, one or more substances which are reactive with KRT19 may be an RNA or DNA complementary to RNA or DNA of KRT19, and an antibody which binds to KRT19 protein and the reagent for detecting reaction products may be a nucleic acid or protein marker and a color developing reagent.

For example, in the case that the kit is applied for PCR amplification process, the kit of the present invention may optionally include reagents required for PCR amplification, for example, buffer solution, DNA polymerases (for example, heat-stable DNA polymerases obtained from *Thermus aquatics* (Taq), *Thermus thermophilus* (Tth), *Thermus filiformis* (Tfi), *Thermis flavus* (TA, *Thermococcus literalis* (Tli) or *Pyrococcus furiosus* (Pfu)), DNA polymerase cofactors, and dNTPs. In the case that the kit of the present invention is applied for immunoassay, the kit of the present invention may optionally include secondary antibodies and a substrate for a label. The kit of the present invention may be manufactured in a number of separate packages or compartments including the above reagent components.

EXAMPLES

Hereinafter, the present invention will be described in more detail by way of examples. The examples are provided for illustrative purposes only and thus, it would be obvious to those skilled in the art that the scope of the present invention is not construed to be limited by the examples.

Preparation and Cell Culture

Human breast cancer cell lines MCF-7 vec, MCF-7 HER2, BT474, SKBr3, Jimt-1 and human embryonic kidney cell line 293T were purchased from American Type Culture Collection (ATCC, Manassas, Va.) and maintained in RPMI 1640 or DMEM media supplemented with 10% FBS (Sigma, St Louis, Mo.) and 1 mg/mL penicillin/streptomycin (Invitrogen, Grand Island, N.Y.) in a 37° C., 5% $CO_2$ incubator.

Example 1

Determination of Relation of HER2 and KRT19 Expression

First, the present inventors investigated the expression of mRNA in the above samples selected from patients with RT-PCR (reverse transcriptase-PCR).

Total RNA was extracted using TRIzol (Invitrogen, Carlsbad, Calif., USA) and quality management was carried out with a Agilent 2001 Bioanalyzer (Agilent Technologies, Germany) using the RNA 6000 Nano chips. Then, 1 μg of RNA was used for cDNA synthesis reaction using RNA PCR Core Kit (Roche, Branchburg, N.J., USA). cDNA was used for each RT-PCR reaction. RT-PCR program was carried out 35 cycles of 95° C. for 30 s, 53° C. for 30 s, and 72° C. for 30 s.

RT-PCR primers used are as follows:

```
HER2 Fwd;
                                        (SEQ ID NO: 1)
AAC TGC ACC CAC TCC TGT GT

HER2 Rev;
                                        (SEQ ID NO: 2)
TGA TGA GGA TCC CAA AGA CC human KRT19 Fwd;
                                        (SEQ ID NO: 3)
GCA CTA CAG CCA CTA CTA CAC GA human KRT19 Rev;
                                        (SEQ ID NO: 4)
CTC ATG CGC AGA GCC TGT T mouse KRT19 Fwd;
                                        (SEQ ID NO: 5)
TGC TGA AGC CAC CTA CCT TG mouse KRT19 Rev;
                                        (SEQ ID NO: 6)
ATA CTC CTG GTT CTG GCG CT human Actin Fwd;
                                        (SEQ ID NO: 7)
GCT CGT CGT CGA CAA CGG CTC human Actin Rev;
                                        (SEQ ID NO: 8)
CAA ACA TGA TCT GGG TCA TCT TCT C mouse Actin Fwd;
                                        (SEQ ID NO: 9)
TTC TTT GCA GCT CCT TCG TTG CCG mouse Actin Rev;
                                        (SEQ ID NO: 10)
TGG ATG GCT ACG TAC ATG GCT GGG
```

Next, Western blot analysis was carried out.

Whole cell extracts were prepared with a RIPA (radioimmunoprecipitation assay) lysis buffer (50 mmol/L Tris-HCl, pH 7.4, 150 mmol/L NaCl, 1% Nonidet P-40, 0.25% sodium deoxycholate, and 1 mmol/L phenylmethane-sulfonylfluoride containing protease inhibitor (Roche, Mannheim, Germany).

Protein concentration was measured using BCA protein assay kit (Pierce, Rockford, Ill.) and the absorbance of protein sample was measured at 570 nm using VICTOR3™ Multilabel Plate Reader (PerkinElmer, Waltham, Mass.).

The RIPA lysates containing 10 μg or 15 μg of protein were separated by SDS-PAGE and transferred onto polyvinylidene difluoride membrane (Amersham Hybond™-P, Little Chalfont, Buckinghamshire, UK) and maintained overnight in 5% skim milk (BD Biosciences, San Jose, Calif.) in TBS solution containing 0.05% Tween-20 (USB Corporation, Cleveland, Ohio) to protect against non-specific binding. The membranes were incubated with each primary antibody (HER2, KRT19, and actin) and HRP-conjugated secondary antibody (Pierce, Rockford, Ill.).

ECL plus Western blotting detection system (Amersham, Buckinghamshire, UK) was used for detecting immobilized certain antigens which were bound to HRP (horseradish peroxidase)-labeled antibodies. The membranes were exposed to LAS 3000 (Fuji Photo Film Co. LTD, Japan).

The above results of RT-PCR and Western blot analysis were shown in FIG. 1.

Figure 1B:
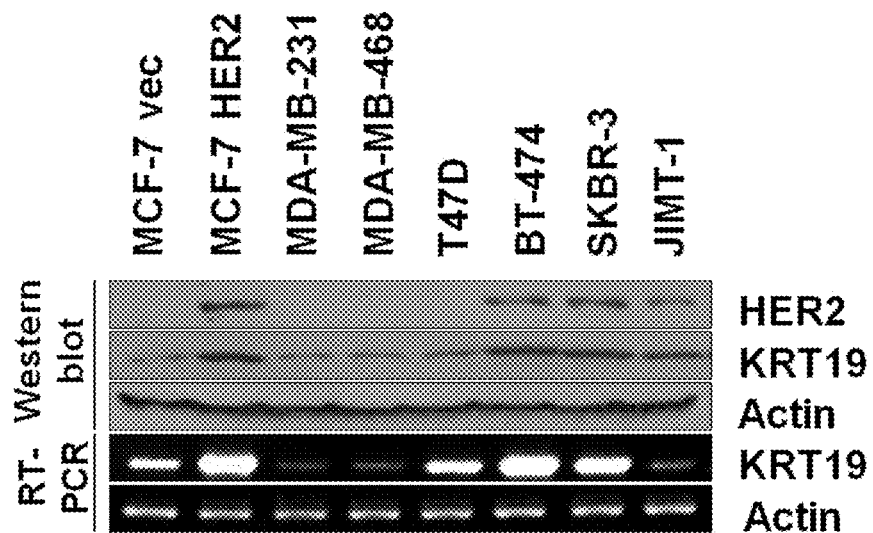
Figure 1C:
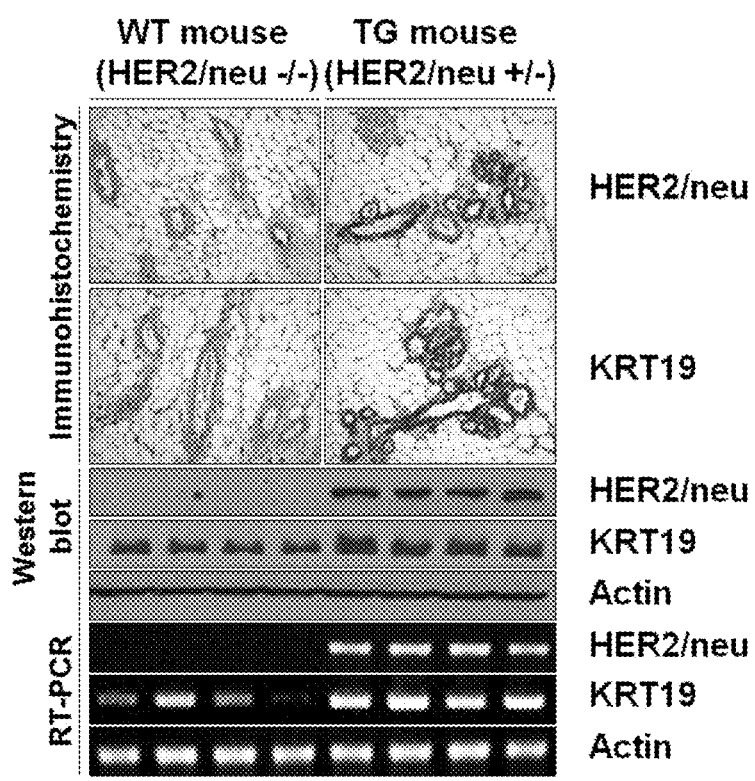
FIGS. 1C and 1D is the results of immunohistochemistry, RT-PCR and Western blot analysis of the expression relation between HER2 and KRT19 in mammary gland tissue of a transgenic mouse (FIG. 1C) and in a tissue of a breast cancer patient (FIG. 1D).
Figure 1D:
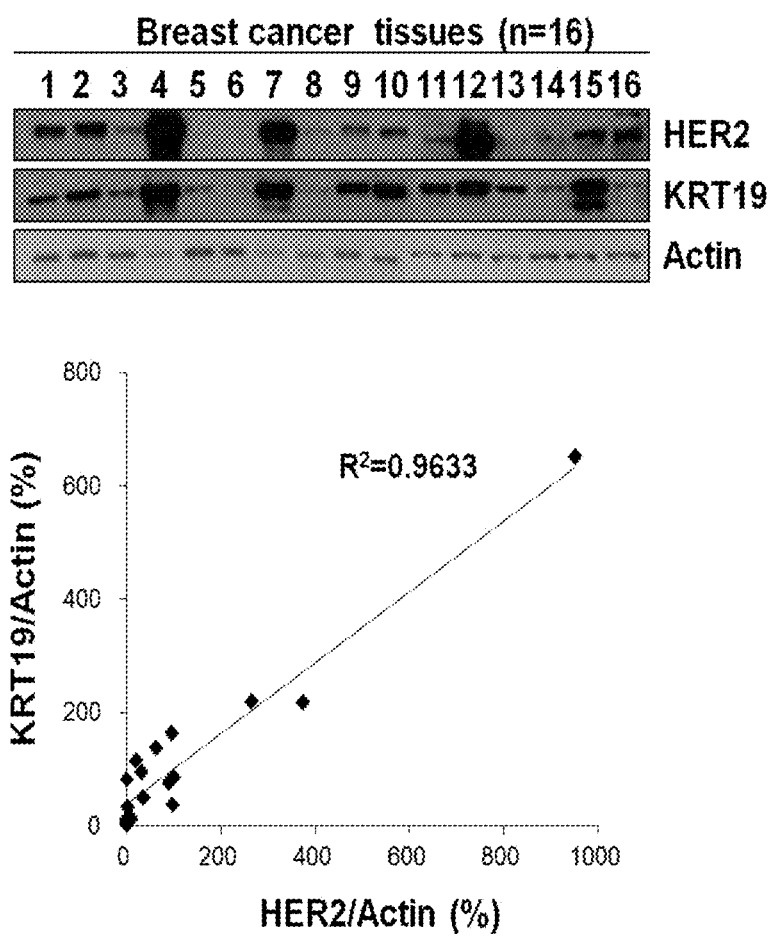

First, it was found that KRT19 was expressed along with HER2 not only in MCR-7 HER2 cell line (FIG. 1A), but also in other breast cancer cell lines (FIG. 1B). Moreover, HER2 and KRT19 were concomitanly expressed in a mammary gland tissue of a transgenic mouse (Jackson Laboratory, ://www.jax.org, FIG. 1C) and in a tissue of a breast cancer patient (Cancer Research Institute, Seoul National University, H-0512-502-163, FIG. 1D).

From the results, it was found that in a cell line overexpressing HER2, KRT19 is also overexpressed.

Example 2

Regulatory Mechanism of the Expression of KRT19 Which is Expressed by HER2

To investigate the regulatory mechanism of the expression of KRT19 which is expressed by HER2, the present inventors carried out RT-PCR and Western blotting using kinase inhibitors as described in Example 1.

ZD1839 is a HER2 inhibitor, U0126 is a MEK inhibitor, Akt I#8 is an Akt inhibitor, SB203580 is a p38 MAPK inhibitor, and LY294002 and Wortmannin were PI#K inhibitors.

Luciferase assay was carried out to observe the transcriptional activity of KRT19. The expression vector for luciferase in which the part of KRT19 promoter was encoded (pK19-1970-LucReporter) was provided by Dr. Anil K Rustgi at University of Pennsylvania. MCF-7 vec and MCR-7 HER2 cell lines were transfected with Lipofectamine (Invitrogen, Grand Island, N.Y.), and 293T cell line was transfected by a calcium phosphate transfection method. The rest experimental procedure was carried out using Dual-Luciferase Reporter Assay System provided by Promega.

The results were shown in FIG. 2.

Figure 2A:
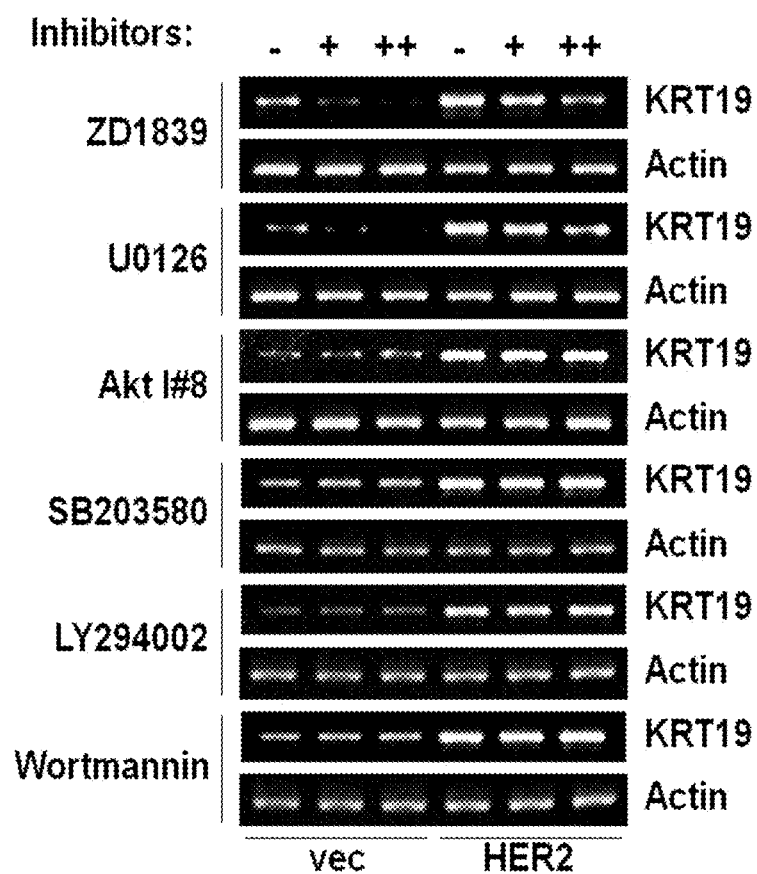
FIG. 2A is the results of RT-PCR analysis of KRT19 mRNA level in the HER2-overexpressing cell lines treated with/without HER2 inhibitor and kinase inhibitor.

First, as shown in FIG. 2A, the expression of KRT19 at the mRNA level was increased in the HER2-overexpressing cell lines, and this was suppressed by a HER2 inhibitor ZD1839 and an inhibitor of MEK/ERK which is one of HER2 downstream enzymes, U0126. However, the other inhibitors failed to exert any effect (the results were obtained from the experiments using MCF-7 vec and MCF-7 HER2).

Figure 2B:
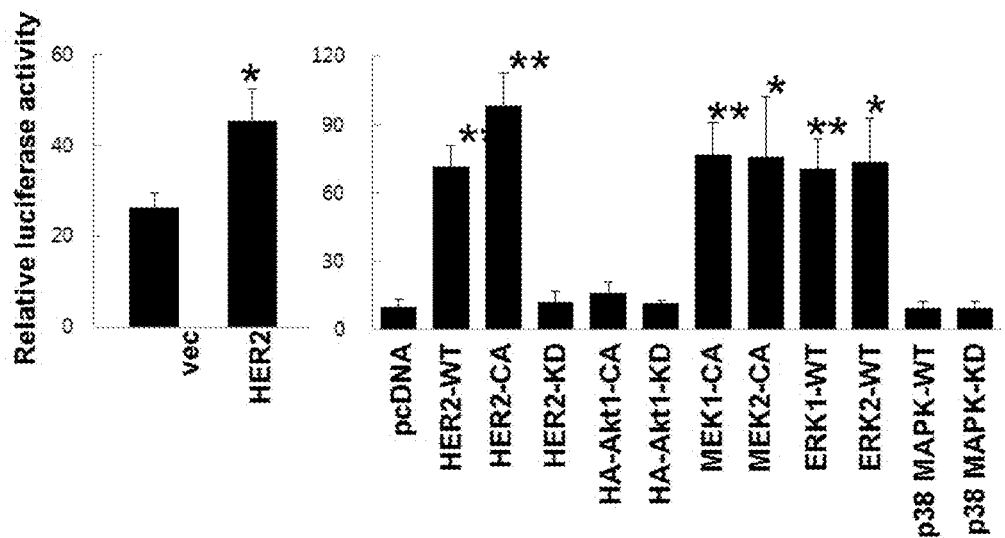
FIG. 2B is the result of luciferase assays on the propter activity of KRT19.

As shown in FIG. 2B, the results of luciferase assays on the promoter activity of KRT19 showed that the promoter activity of KRT19 was increased by HER2 and its downstream enzyme MEK/ERK.

Figure 2C:
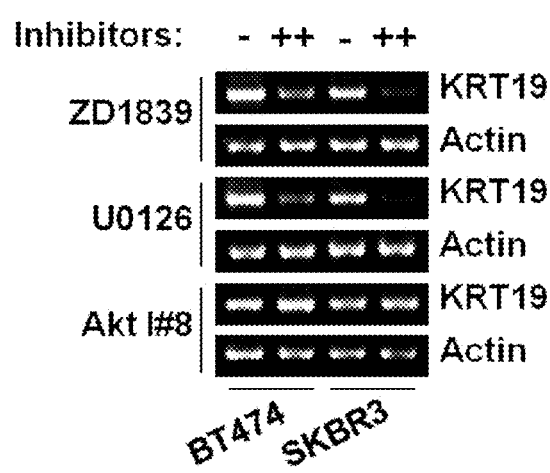
FIG. 2C is the results of RT-PCR analysis expression of KRT19 at the mRNA level was increased in the HER2-overexpressing cell lines (BT474, SKBR3) with HER2 inhibitor or inhibitor of MEK/ERK.

Also, as shown in FIG. 2C, the expression of KRT19 at the mRNA level was increased in the HER2-overexpressing cell lines, and this was suppressed by a HER2 inhibitor ZD1839 and an inhibitor of MEK/ERK which is one of HER2 downstream enzymes, U0126, but the other inhibitors failed to exert any effect (the results were obtained from the experiments using BT-474 and SKBr3, which overexpress endogenous HER2).

Figure 2D:
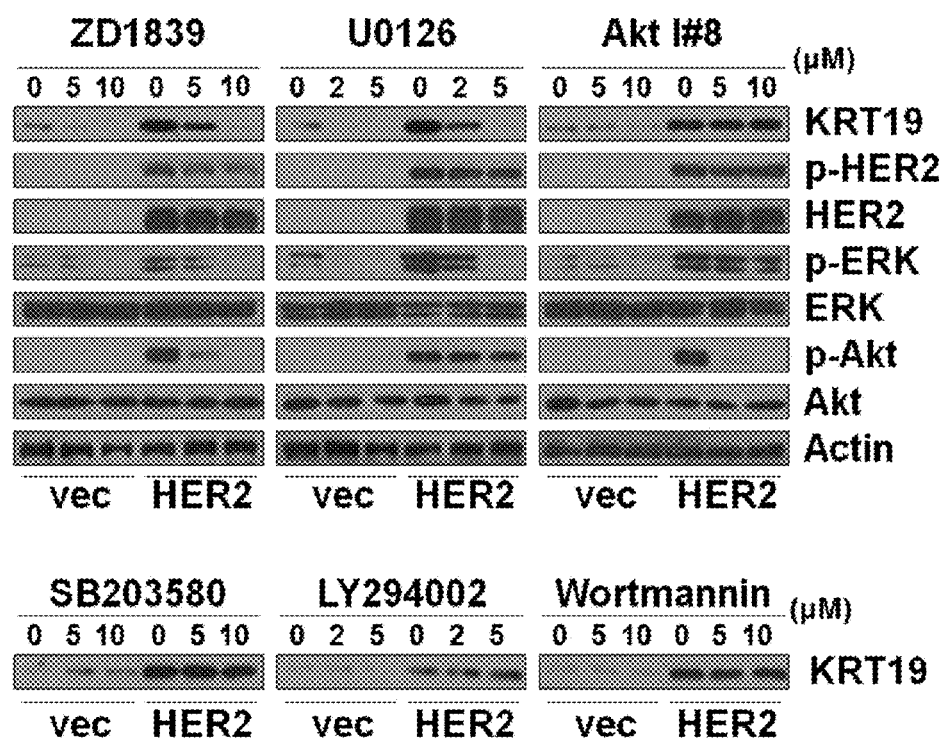
FIG. 2D is the result of Western Blot analysis of KRT19 expression in the HER2-overexpressing cell lines with HER2 inhibitor or inhibitor of MEK/ERK.
Figure 2E:
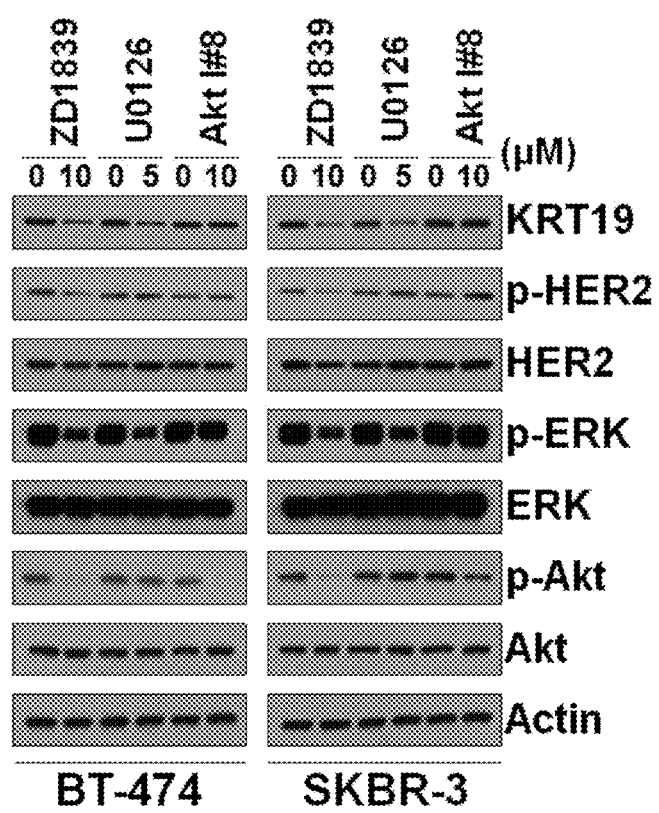
FIG. 2E is the Western Blot analysis of KRT19 in the HER-2 overexpressing cell lines (BT474, SKBR3)

Likewise, as shown in FIG. 2D, the expression of KRT19 at the protein level was increased in the HER2-overexpressing cell lines, and this was suppressed by a HER2 inhibitor ZD1839 and an inhibitor of MEK/ERK which is one of HER2 downstream enzymes, U0126, but the other inhibitors failed to exert any effect (the results were obtained from the experiments using MCF-7 vec and MCF-7 HER2). Also, as shown in FIG. 2E, the expression of KRT19 at the protein level was increased in the HER2-overexpressing cell lines, and this was suppressed by a HER2 inhibitor ZD1839 and an inhibitor of MEK/ERK which is one of HER2 downstream enzymes, U0126, but the other inhibitors failed to exert any effect (the results were obtained from the experiments using BT-474 and SKBr3, which overexpress endogenous HER2).

Figure 2F:
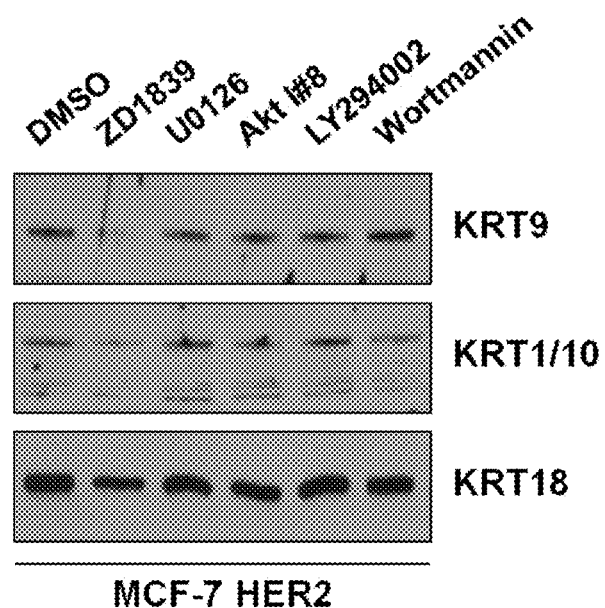
FIG. 2F is the result of Western Blot analysis of KRT19 isotype expression with HER2 inhibitor or inhibitor of MER/ERK.

In addition, as shown in FIG. 2F, the expression of KRT19 isotypes was increased by HER2, however, it was not suppressed by a HER2 inhibitor ZD1839 and an inhibitor of MEK/ERK which is one of HER2 downstream enzymes, U0126.

From these results, it was found that the expression of KRT19 is suppressed by the inhibitor of MEK/ERK, one of HER2 downstream enzymes, and this suggests that the expression of KRT19 and the MEK/ERK signaling pathway are deeply related to each other.

Example 3

Ser35 Phosphorylation of KRT Mediated by Akt, a HER2 Downstream Enzyme

Co-immunoprecipitation assay, in vitro kinase assay, and in vivo labeling were carried out to observe Akt mediated Ser35 phosphorylation of KRT19.

After Extracts were obtained from cells as described in Western blot assay, immunoprecipitation was carried out with KRT19 antibody and protein A sepharose. The rest experimental procedure was carried out identically to Western blot assay, and an antibody which can bind specifically to substrates of Akt was used as a primary antibody.

To perform in vitro kinase assay, KRT19 was cloned with a GST fusion protein into an expressible vector and transfected into $E.\ coli$, and GST-KRT19 fusion protein was obtained using a sonicator. HA-tagged Akt construct was transfected into 293T cell line, and immunoprecipitation was carried out with HA antibody to obtain HA-Akt protein.

To the obtained GST-KRT19 and HA-Akt proteins, a kinase reaction buffer (25 mM Tris-HCl, pH 7.5, 5 mM β-glycerophosphate, 0.1 mM sodium orthovanadate, 2 mM dithiothreitol, 200 μM ATP, 10 mM magnesium chloride) and 10 μCi [γ32-P]ATP (Amersham, Buckinghamshire, UK) were added and incubated at room temperature for 30 min, and then, SDS-PAGE and autoradiography were carried out.

To perform in vivo labeling assay, Akt and KRT19 were co-transfected into 293T cell line. After transfection, phosphate-depleted medium was used for cell culture, and [$^{32}$P] orthophosphate 500 μCi/ml was treated to cells, and cells were cultured for 18 h in an incubator. Immunoprecipitation was carried out using KRT19 antibody, and SDS-PAGE and autoradiography were carried out.

Figure 3A:
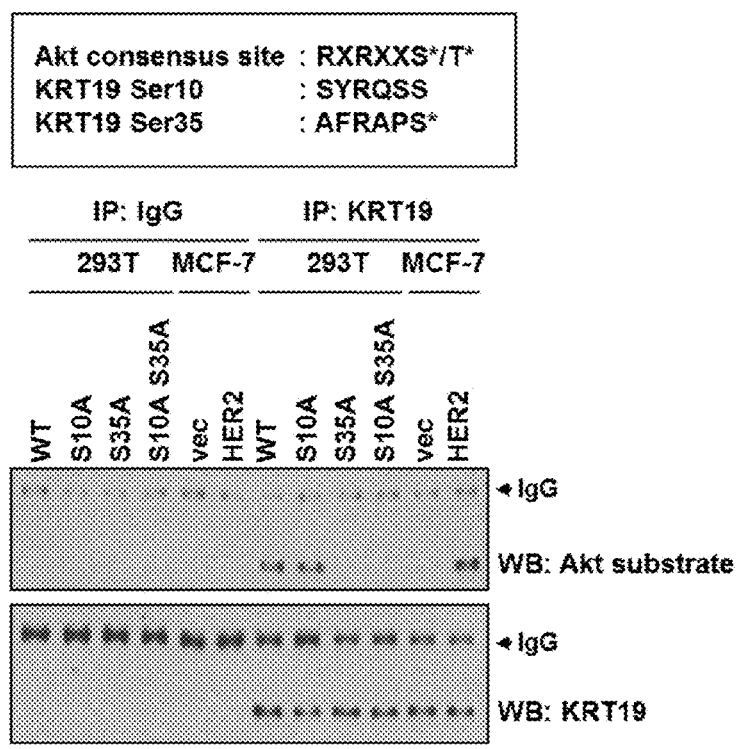
FIG. 3A is the results of co-immunoprecipitation assay (co-IP) using an antibody recognizing Akt-specific phosphorylated sequence.
Figure 3B:
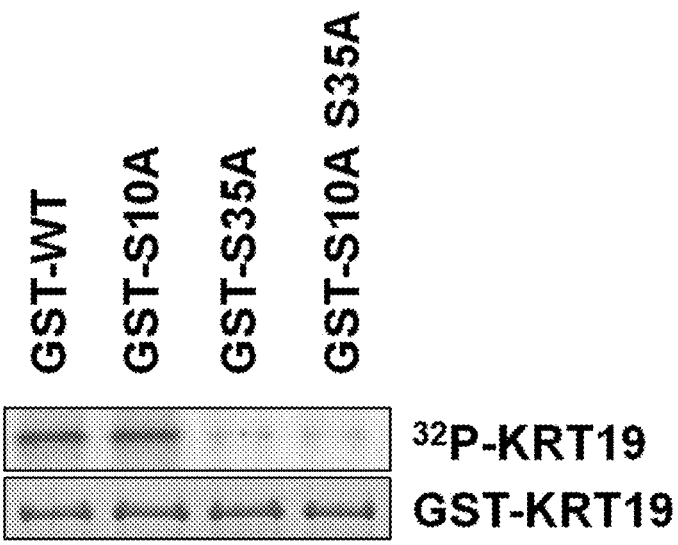
FIG. 3B is the result of in vitro kinase analysis using GST-KRT.
Figure 3C:
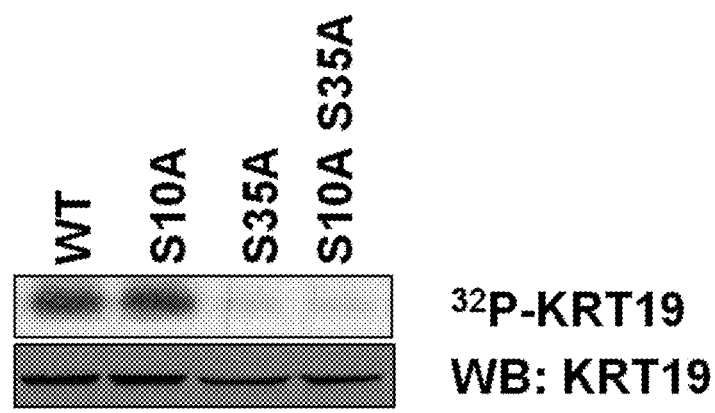
FIG. 3C is the result of in vivo labeling analysis for observation of Akt-mediated Ser 35 phosphorylation of KRT19.

Consequently, as shown in FIG. 3, the result obtained using an antibody recognizing Akt-specific phosphorylated sequence (A), the result of in vitro kinase assay using GST-KRT19 (B), and the result of in vivo [$^{32}$P] orthophosphate labeling showed that Akt mediated Ser35 phosphorylation of KRT.

Example 4

Shape Modification of KRT19 Induced by Akt, a HER2 Downstream Enzyme

The shape of KRT19 was observed using an immunocytochemistry assay.

Cells were fixed in about 4% paraformaldehyde for 10 min, and then permeabilized in 0.1% Triton X-100 for 10 min. After blocking with 3% skim milk, the rest experimental procedure was carried out identically to Western blot assay. IgG-Oregon Green by which green fluorescence can be observed, and IgG-Cy3 by which red fluorescence can be observed, and the like were used as secondary antibodies.

The results were shown in FIG. 4. The results of comparing MCF-7 vec with MCF-7 HER2 and observing HER2 expression-induced cellular distribution pattern of KRT19 showed that the distribution pattern of KRT19 was shape-modified from a filamentous shape to a granulous shape (FIG. 4A and FIG. 4B).

Figure 4A:
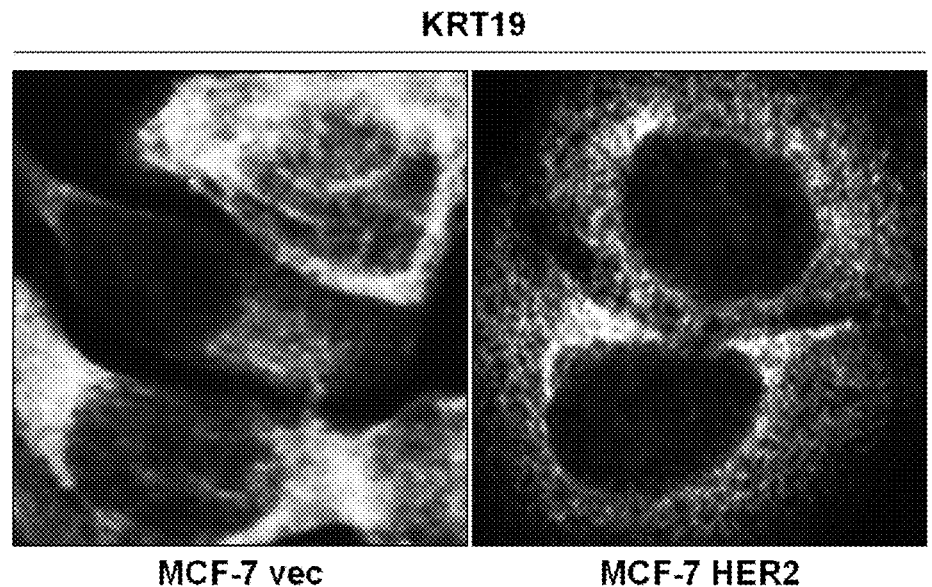
FIG. 4A is the results of immunocytochemistry assay for observation of the shape of KRT19 in MCF-7 vec or MCF-7 HER2 expressed cell.
Figure 4B:
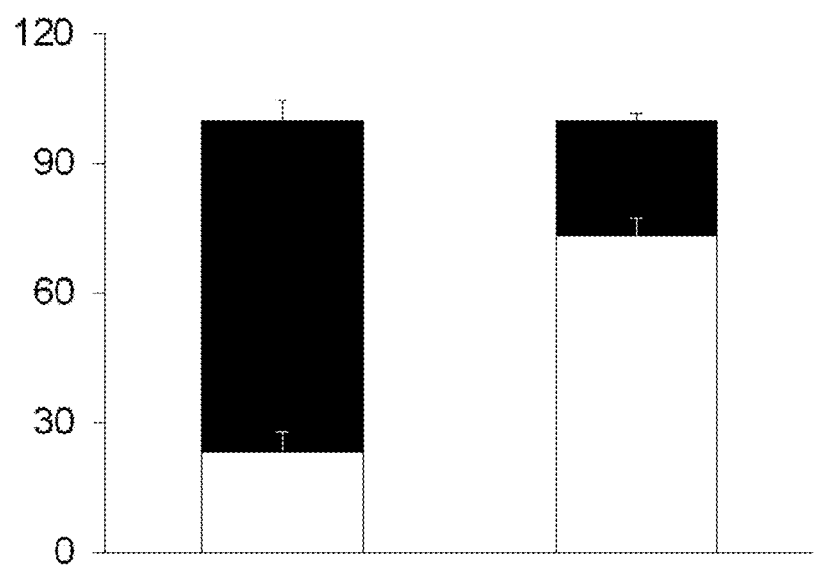
FIG. 4B. is the result of immunocytochemistry assay morphological analysis of HER2 overexpressing.
Figure 4C:
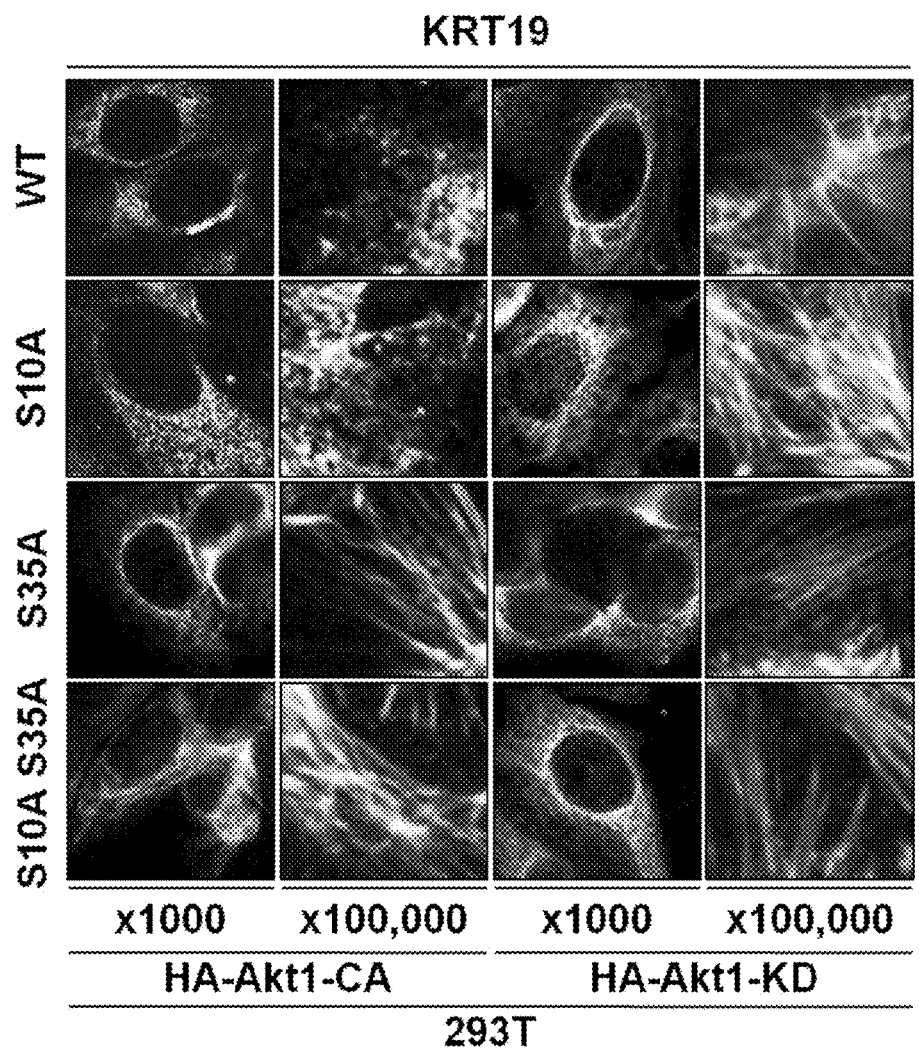
FIG. 4C. is the result of immunocytochemistry assay in 293T cell with Akt-induced Ser35 phosphorylation.
Figure 4D:
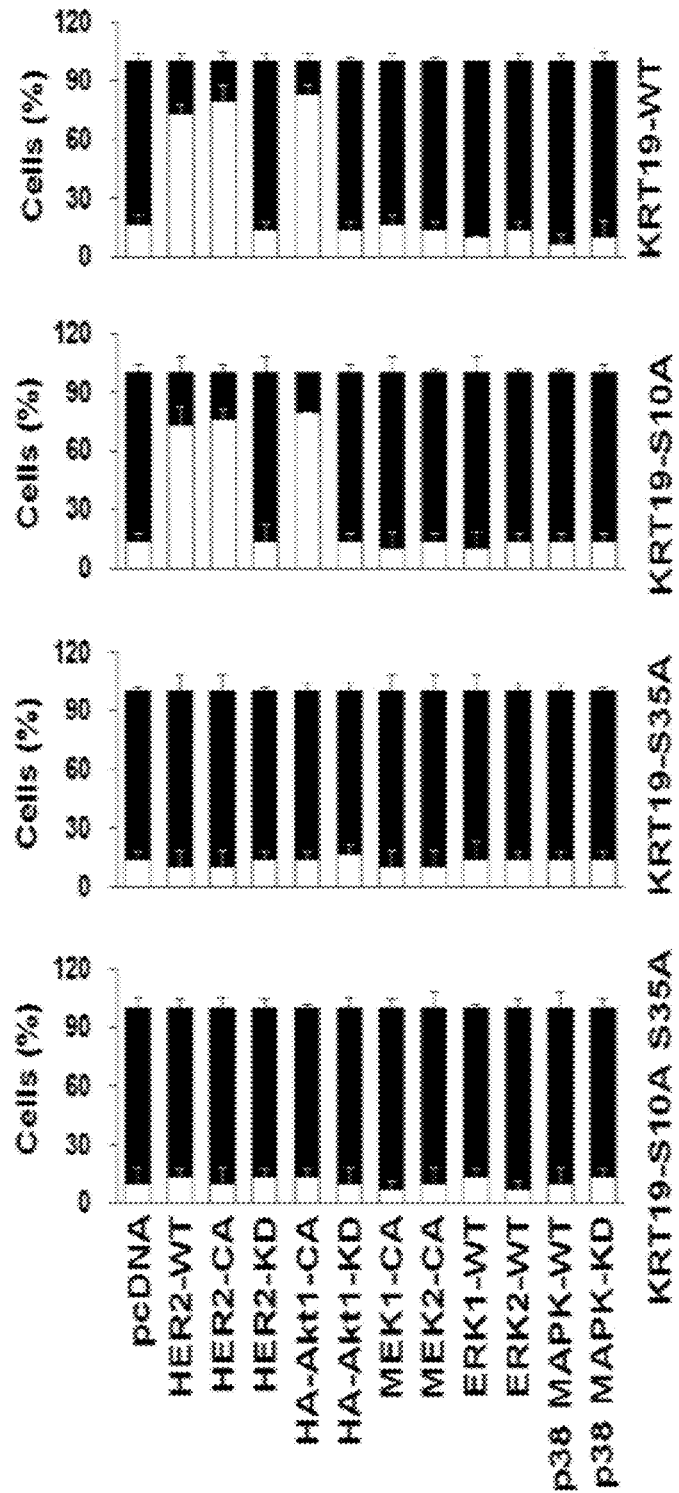
FIG. 4D is the quantitative analysis of FIG. 4C.

Furthermore, experiments with mutants of KRT19 showed additionally that cellular distribution pattern of KRT19 was modified from a filamentous shape to a granulous shape by a HER2 downstream enzyme Akt-induced Ser35 phosphorylation (FIG. 4C).

Example 5

Relocalization of KRT19 to Cell Membrane

An immunocytochemistry assay was used as in Example 4, however, the example is for the observation of protein expression outside of cell membrane and the permeabilization procedure was excluded and the rest experimental procedure was carried out identically to Example 4.

Cells were separated into membrane and cytoplasm fraction and a ultracentrifuge was used for the observation of protein expression. Cells were centrifuged at 100,000 g, and the supernatant and pellet were fractionated into cytoplasm fraction and cell membrane fraction, respectively. The rest experimental procedure was carried out identically to Western blot assay.

The results were shown in FIG. 5.

Figure 5A:
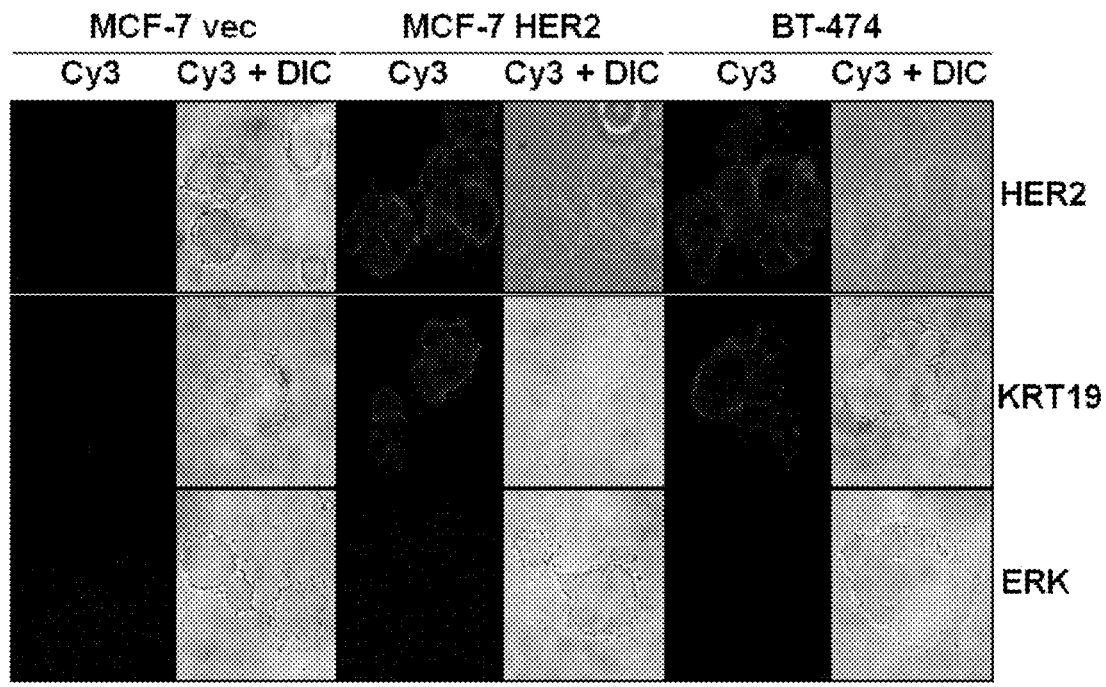
FIG. 5A is the results of immunocytochemistry assay for observation of protein expression outside of cell membrane in MCF-7 vec, MCF-7 HER2, and BT-474 cells.
Figure 5B:
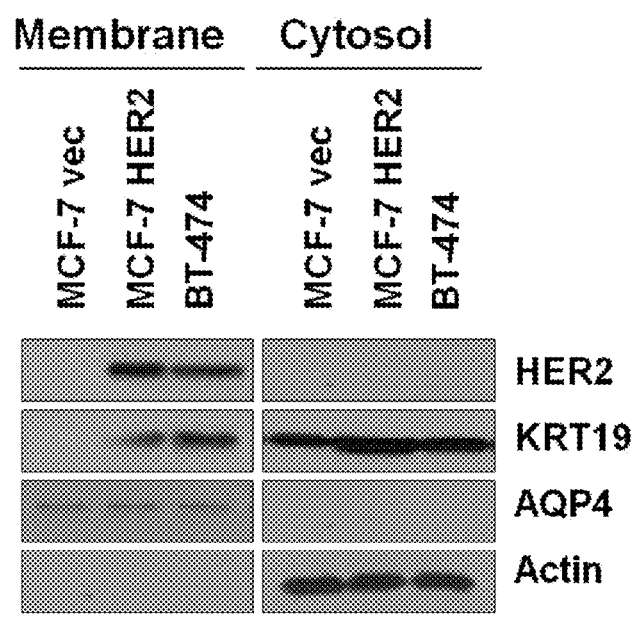
FIG. 5B is the result of cell fraction assay of KRT19 expression outside of cell membrane.
Figure 5C:
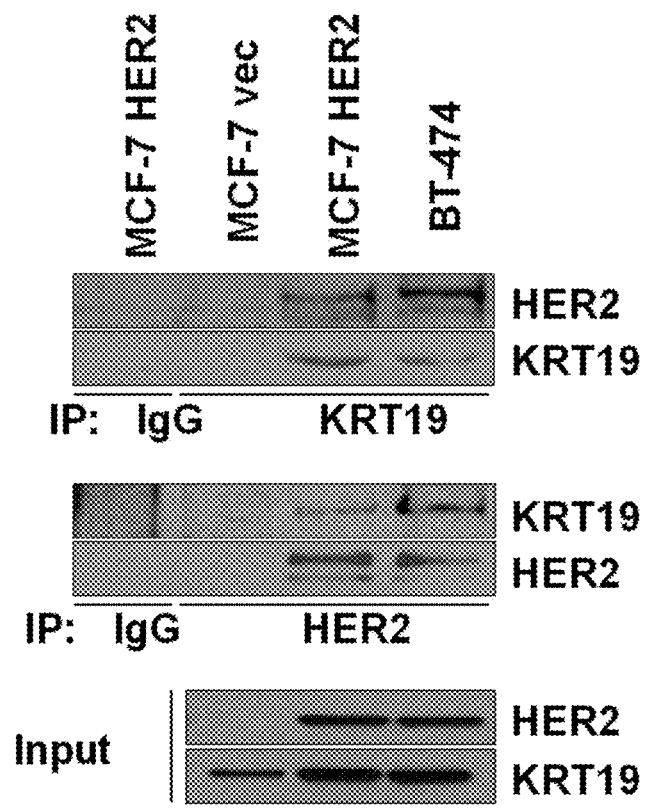
FIG. 5C is the result of co-immunoprecipitation assay for HER2 and KRT19.
Figure 5D:
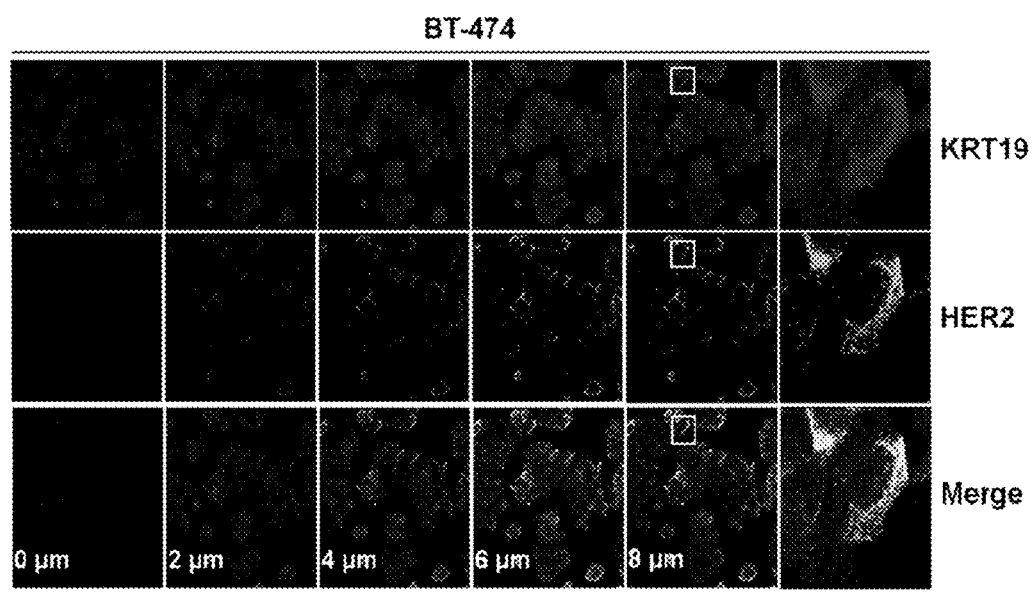
FIG. 5D is the result of immunocytochemistry assay for HER2 and KRT19.

First, the comparison of the results for MCF-7 vec to MCF-7 HER2, BT-474 cells showed that KRT19 was relocalized at the cellular surface by HER2 expression through cell surface staining (FIG. 5A). In addition, by using a cell fractionation assay, it was found that KRT19 was relocalized to cell membrane fraction (FIG. 5B), and by using a co-immunoprecipitation assay, it was found that HER2 and KRT19 were associated with each other (FIG. 5C). With an immunocytochemistry assay, it was found that HER2 and KRT19 were localized in the same site (FIG. 5D).

Figure 6:
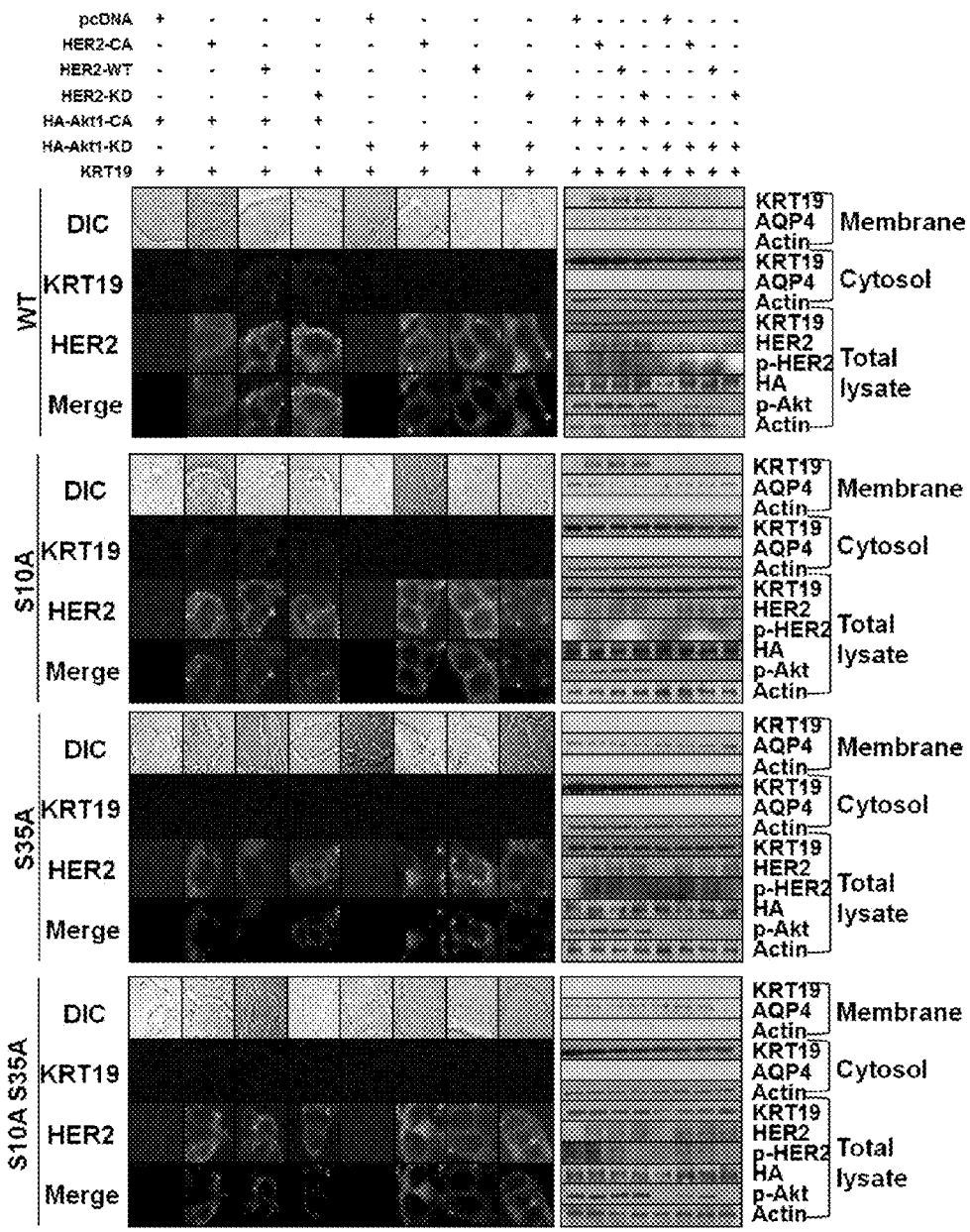
FIG. 6 is the results of immunocytochemistry and Western blot analysis to confirm the relocalization to cell membrane by Akt-mediated Ser 35 phosphorylation of KRT19.

In addition, as shown in FIG. 6, it was found that Akt-mediated Ser35 phosphorylation of KRT19 is needed for the relocalization to cell membrane.

These results mean that KRT19 is relocalized to cell membrane through a HER2 downstream enzyme Akt-induced Ser35 phosphorylation.

Example 6

Stabilization of HER2 by KRT19 which was Relocalized to Cell Membrane

After confirming that KRT19 exists on the cell membrane, KRT19 was knocked down by KRT19-specific shRNA, purchased from Santa Cruz Biotechnology (catalog number sc-35152-SH), and treated with a protein synthesis inhibitor, cycloheximide (CHX).

Consequently, as shown in FIG. 7, as KRT19 was knocked down by shRNA, the amount of HER2 protein was decreased in a time dependent manner after treatment with CHX. However, in the case of treatment with Akt inhibitor only, the amount of HER2 protein was not inhibited, since Ser35-phosphorylated and HER2-bound KRT19 still existed. However, in the case that an Akt inhibitor and a protein synthesis inhibitor were treated concomitantly, the amount of HER2 was decreased.

This means that phosphorylated KRT19 is required for the stabilization of HER2.

Figure 7A:
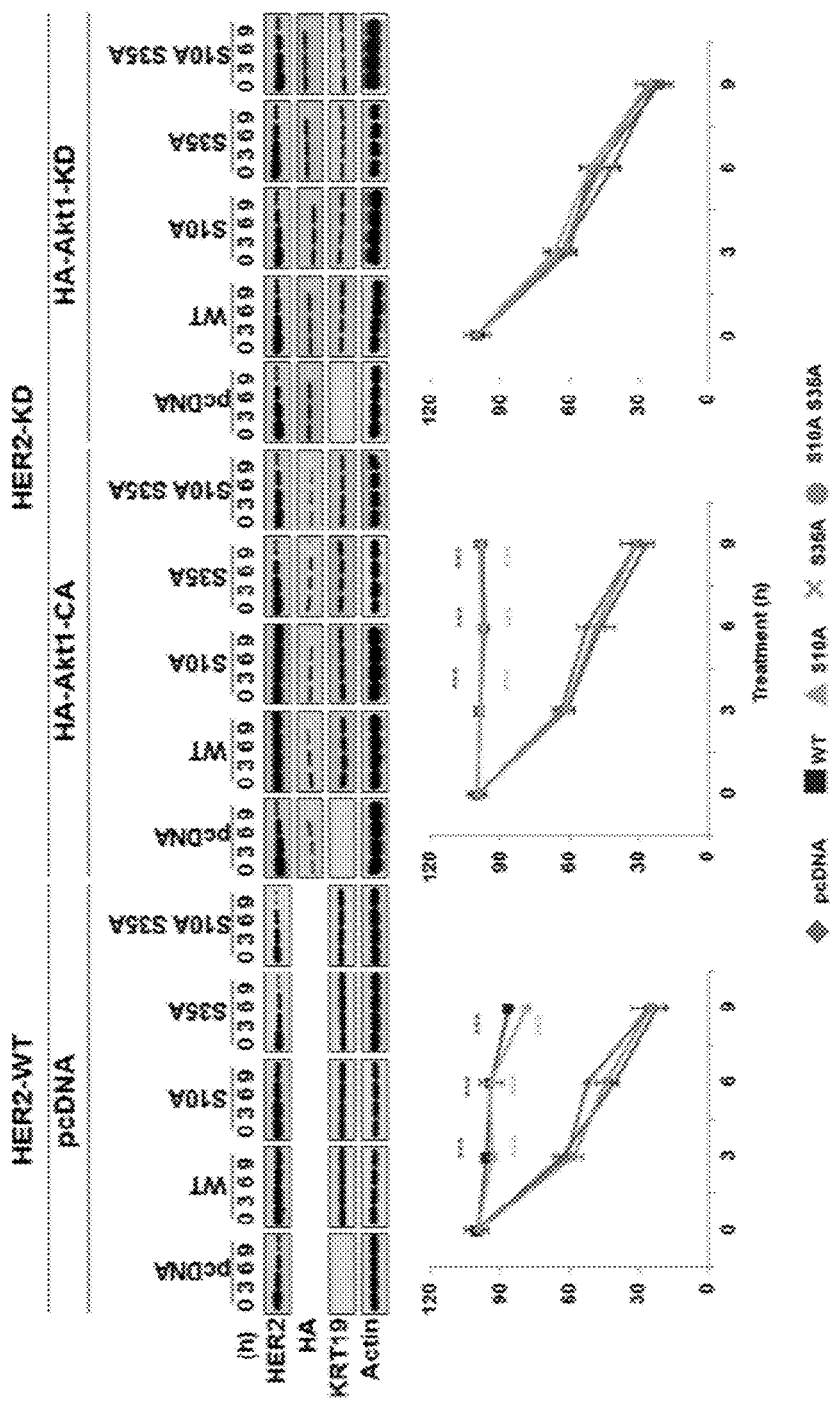
FIGS. 7A and 7B are the results of RT-PCR and Western blot analysis for observation of HER2 stabilization using KRT19 shRNA and protein synthesis inhibitor (CHX).
Figure 7B:
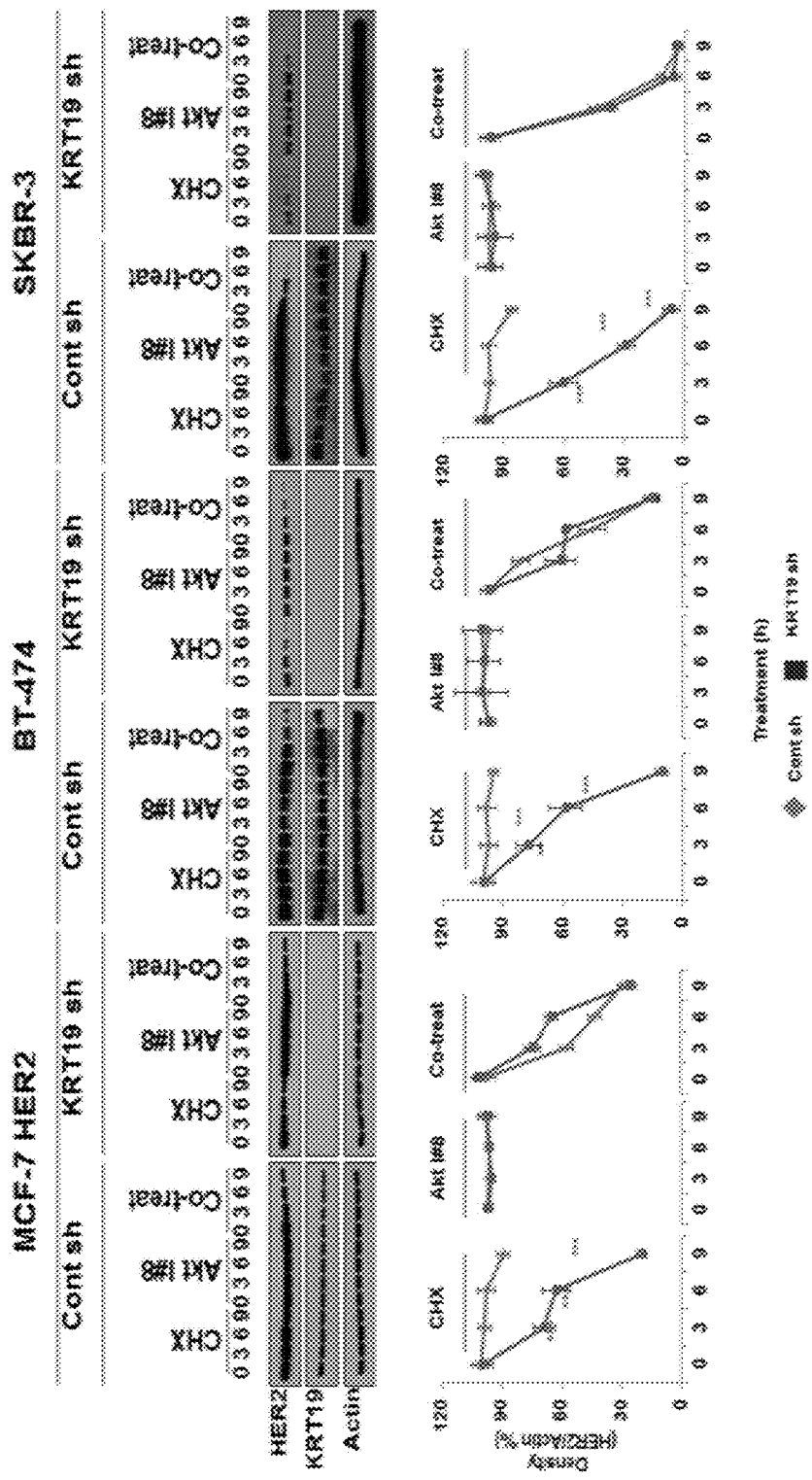
Figure 7C:
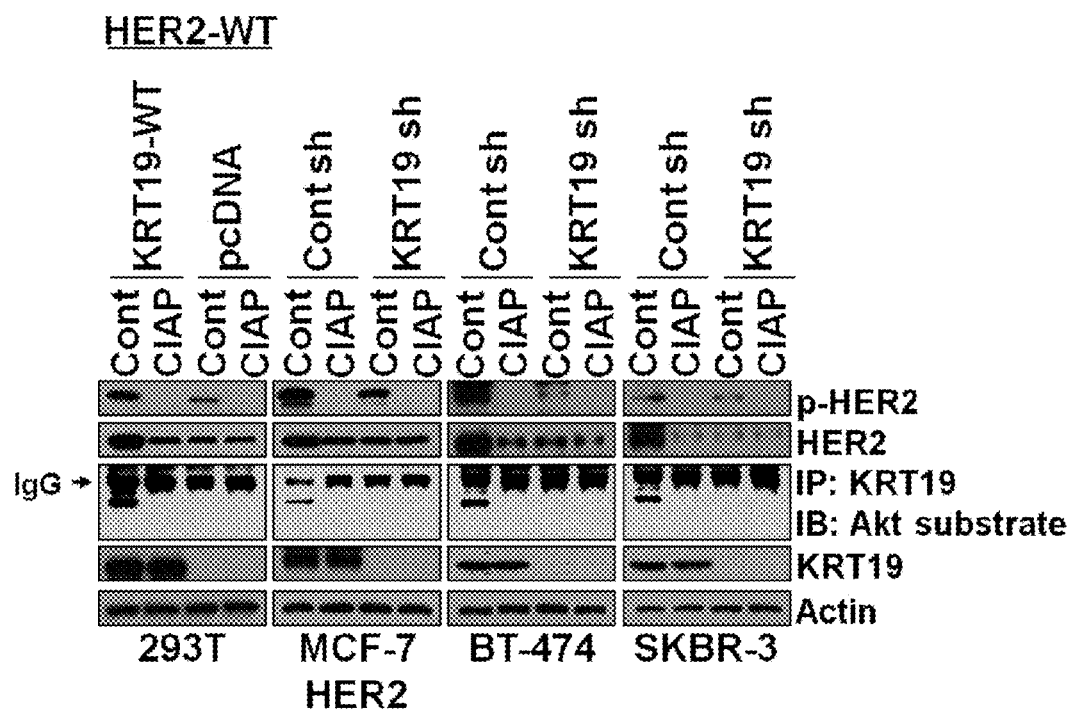
FIG. 7C is the result of immunoprecipitation assay after dephosphorylation of KRT19 using CIAP.

Accordingly, as shown in FIG. 7C, dephosphorylation of KRT19 with CIAP inhibited the stability of HER2.

Figure 7D:
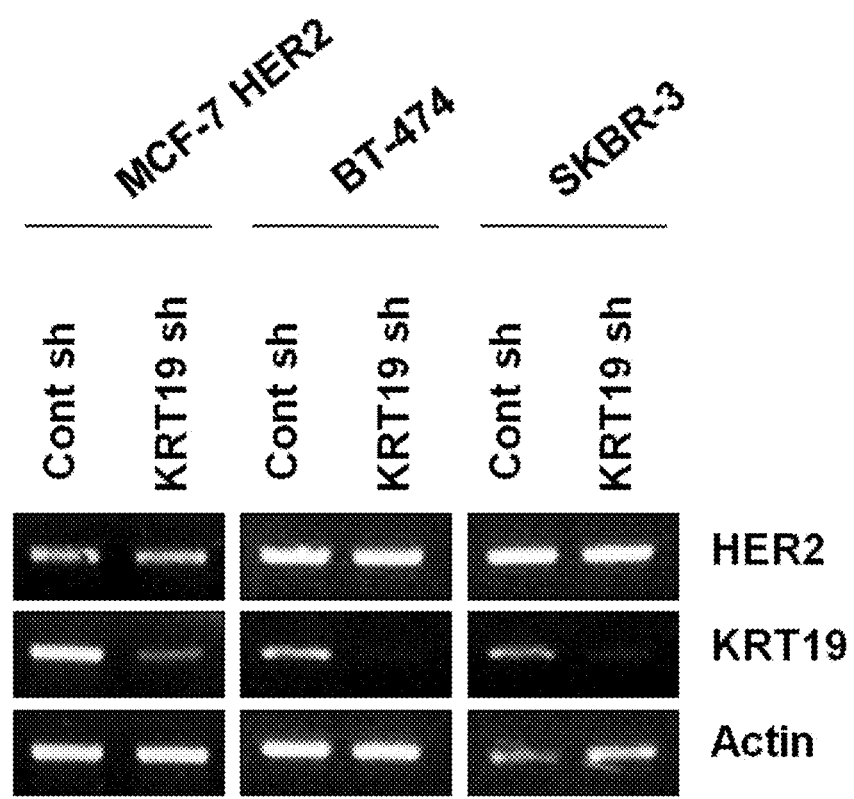
FIG. 7D is the result of RT-PCR analysis for HER2 ubiquitination.

In addition, the regulation of stability of HER2 by KRT19 was carried out at the protein level, and this was confirmed from the unchanged amount of mRNA (FIG. 7D).

Meanwhile, the effect of KRT19 on HER2 ubiquitination was investigated.

Figure 8A:
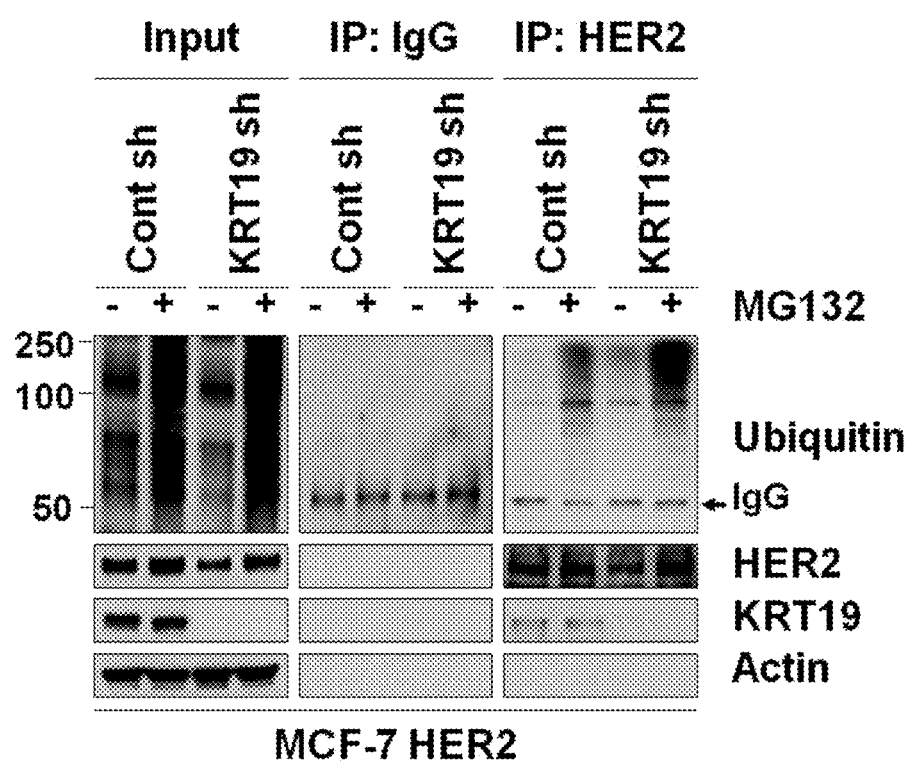
FIG. 8A is the results of Western blot analysis to determine the effect of KRT19 on HER2 ubiquitination.
Figure 8B:
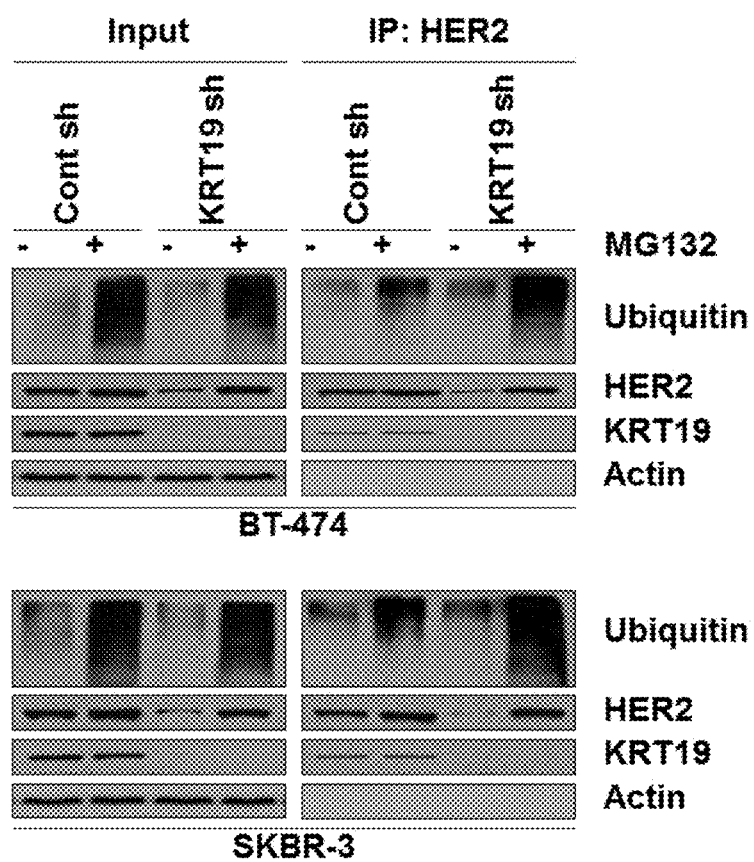
FIG. 8B is the result of Western blot analysis to determine Akt-induced Ser- 35 phosphorylated KRT on Her2 ubiquitination.
Figure 8C:
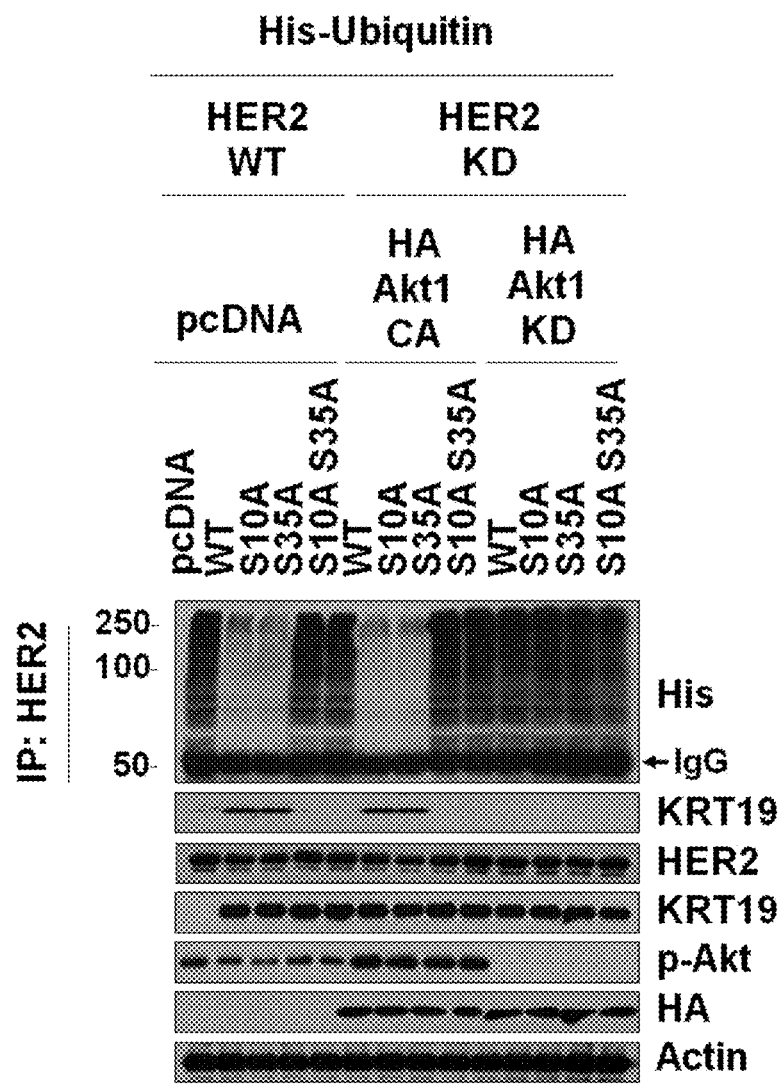
FIG. 8C is the result of immunoprecipitation assay to determine Akt-induced Ser-35 phosphorylated KRT on Her2 ubiquitination.

Consequently, as shown in FIG. 8, when the expression of KRT19 was inhibited, HER2 ubiquitination was increased rapidly (FIG. 8A), and it was found that Akt-induced Ser-35 phosphorylated KRT19 is required for inhibition of HER2 ubiquitination (FIG. 8B, FIG. 8C). This means that KRT19 inhibits ubiquitination, thereby resulting in HER2 stabilization.

Figure 8D:
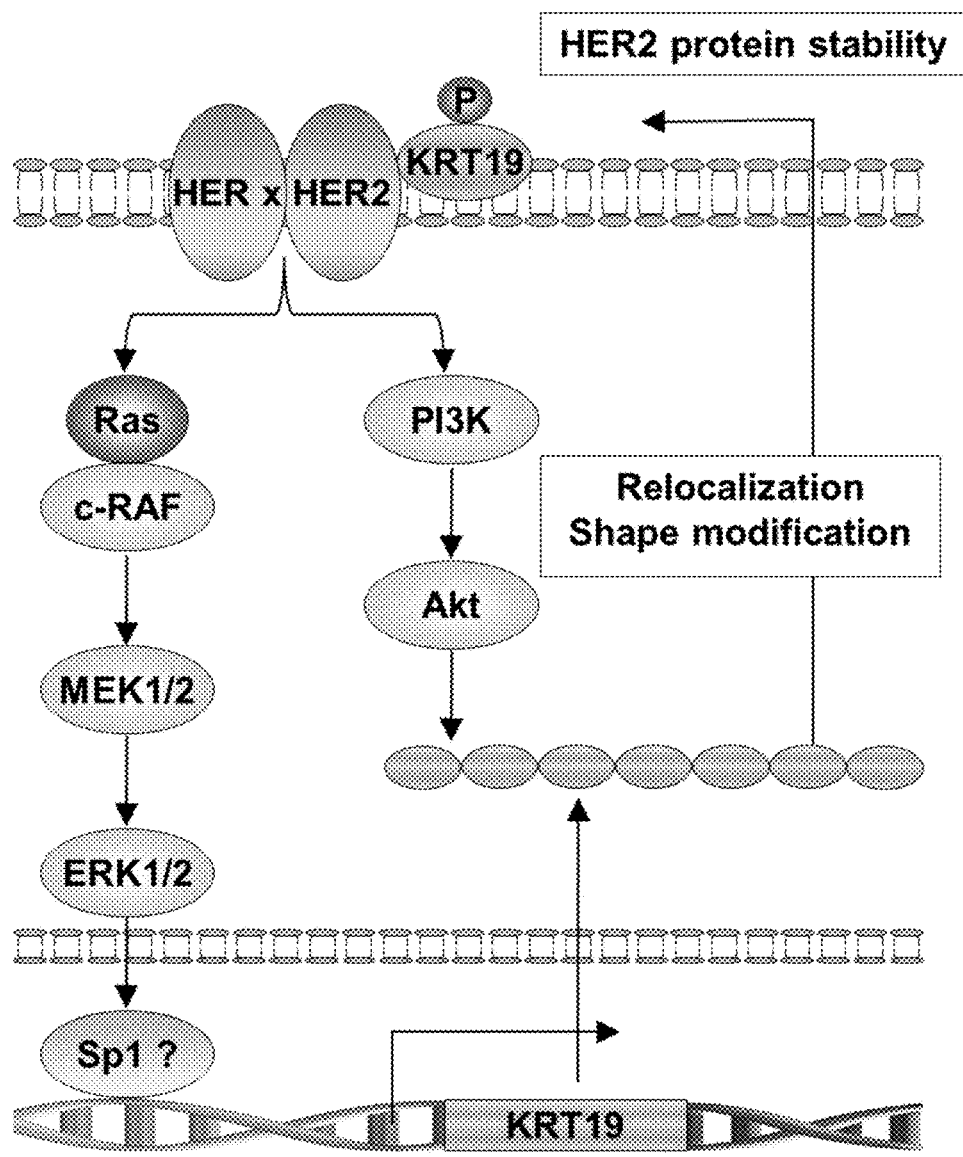
FIG. 8D is the molecular mechanism between KRT19 and HER2.

The molecular mechanism of KRT19 which was confirmed from these results was shown in FIG. 8D.

That is, KRT19, of which the expression is increased at the transcriptional level by a HER2 downstream signaling enzyme MEK/ERK, is phosphorylated on Ser35 by a HER2 downstream signaling enzyme Akt, and is relocalized to cell membrane fraction, and binds to HER2, and then inhibits ubiquitination, and thus, increases HER2 stabilization.

Example 7

Anticancer Effect of KRT19 Antibody

To investigate whether a KRT19-specific antibody inhibits breast cancer cell growth, the present inventors treated the culturing HER2-overexpressing breast cancer cell line BT-474 and Jimt-1 cell line which was known as a Herceptin-resistant cell line with Herceptin (Roche, USA) with a variety of anti-KRT19 antibodies (CBL198 manufactured by Chemicon; 53003, 33120, 331 and 33119 manufactured by Santa Cruz Biotechnology) at the concentration of 10 μg/ml or 20 μg/ml, and carried out a MTT assay and cell-counting assay.

Figure 10:
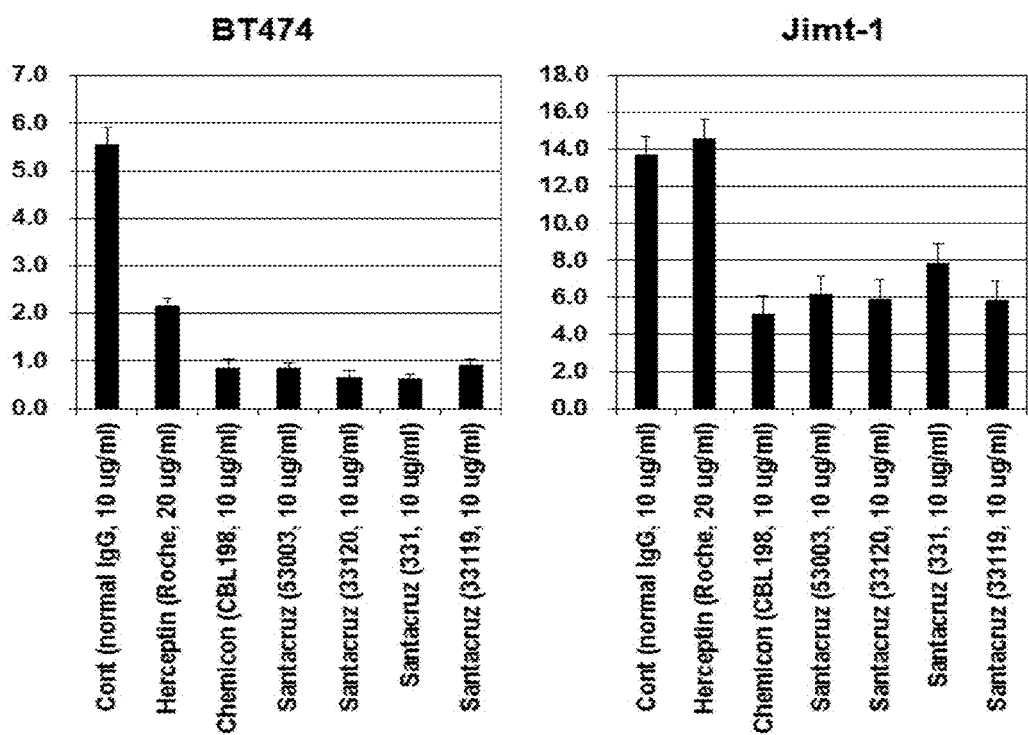
FIG. 10 is the results of a cell counting assay using KRT19 antibodies.

Consequently, it was found that anti-KRT19 antibodies inhibited survival of the HER2-overexpressing cell line BT-474 (FIG. 9A and FIG. 10A). Although Herceptin did not cause any change in Jimt-1 cell line which was known as a Herceptin-resistant cell line, anti-KER19 antibodies caused apoptosis in Jimt-1 cell (FIG. 9B and FIG. 10B). This suggests that even in conventional Herceptin-resistant cancer cell line (Jimt-1), the effect of cancer cell death can be exerted by inhibiting the activity of KRT19, a novel target, which can exert the HER2 expression-inhibitory effect by the present invention, and accordingly, the expression or activity inhibitor of KRT19 can be used as a new anticancer agent (for HER2-positive cancers) which can replace Herceptin and the like. Meanwhile, as shown in FIG. 9, in Herceptin sensitive cells (BT-474), the concomitant treatment with Herceptin and anti-KRT19 antibody did not show difference in effect compared to the single-Herceptin treatment and single-anti-KRT19 antibody treatment, however, in Herceptin-resistant cells (Jimt-1), the concomitant treatment with Herceptin and anti-KRT19 antibody showed better cell death effect than the single-anti-KRT19 antibody treatment. Therefore, the concomitant treatment with Herceptin and anti-KRT19 antibody can be expected to exert better effect on Herceptin-resistant cancers.

Example 8

Preparation of Anti-KRT19 Monoclonal Antibody

Since anti-KRT19 antibodies used in Example 7 were available from Chemicon (USA) and Santa Cruz Biotechnology, the present inventors prepared an anti-KRT19 monoclonal antibody for the mass production of anti-KRT19 antibodies.

Figure 11:
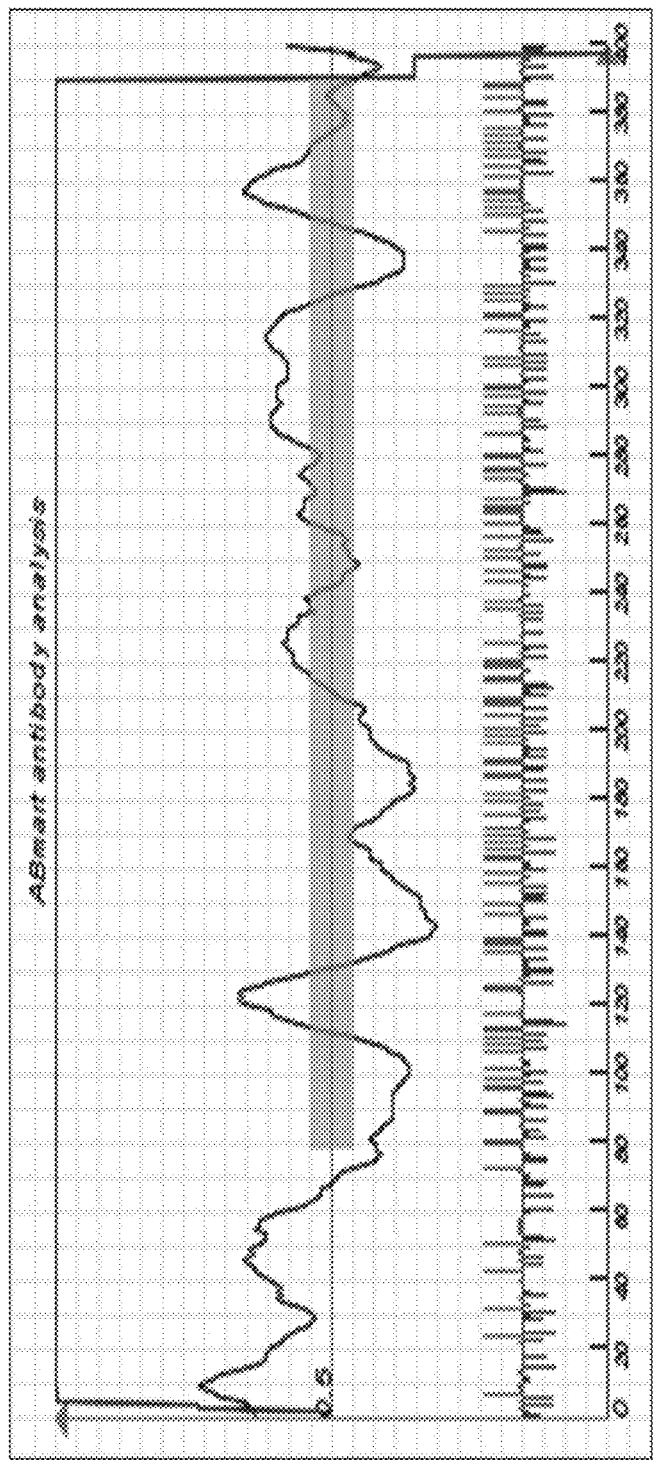
FIG. 11 is the analysis result of KRT19 antibodies including hydrophobic region profile.

The region with low hydrophobicity and high antigenicity has generally high possibility of antibody preparation and high possibility of outward exposure from tertiary structure of protein, and this region was preferentially considered for selection (FIG. 11, thick green line).

Considering all the above details, total four target candidate amino acid sequences were established below:

TABLE 1

| Amino acid sequence information | Amino acid sequence | SEQ ID NO. |
|---|---|---|
| 167 amino acids (7~173) | RQSSATSSFGGLGGGSVRFGPGVAFRAPSIHGGSGGR GVSVSSARFVSSSSSGAYGGGYGGVLTASDGLLAGN EKLTMQNLNDRLASYLDKVRALEAANGELEVKIRD WYQKQGPGPSRDYSHYYTTIQDLRDKILGATIENSRI VLQIDNARLAADDFRTKFETEQ | 11 |
| 253 amino acids (78~330) | GNEKLTMQNLNDRLASYLDKVRALEAANGELEVKI RDWYQKQGPGPSRDYSHYYTTIQDLRDKILGATIENS RIVLQIDNARLAADDFRTKFETEQALRMSVEADINGL RRVLDELTLARTDLEMQIEGLKEELAYLKKNHEEEIS TLRGQVGGQVSVEVDSAPGTDLAKILSDMRSQYEV MAEQNRKDAEAWFTSRTEELNREVAGHTEQLQMSR SEVTDLRRTLQGLEIELQSQLSMKAALEDTLAETEAR | 12 |
| 150 amino acids (1~150) | MTSYSYRQSSATSSFGGLGGGSVRFGPGVAFRAPSIH GGSGGRGVSVSSARFVSSSSSGAYGGGYGGVLTASD GLLAGNEKLTMQNLNDRLASYLDKVRALEAANGEL EVKIRDWYQKQGPGPSRDYSHYYTTIQDLRDKILGA TIENSR | 13 |
| 179 amino acids (215~393) | KKNHEEEISTLRGQVGGQVSVEVDSAPGTDLAKILSD MRSQYEVMAEQNRKDAEAWFTSRTEELNREVAGHT EQLQMSRSEVTDLRRTLQGLEIELQSQLSMKAALEDT LAETEARFGAQLAHIQALISGIEAQLGDVRADSERQN QEYQRLMDIKSRLEQEIATYRSLLEGQEDHYNN | 14 |

Among these, the sequence of total 253 amino acids from 78$^{th}$ amino acid sequence to 330$^{th}$ amino acid sequence was selected for a target of antibody preparation.

The sequence selected as an antigen was prepared through peptide synthesis and injected into the abdominal cavity of a 6-8 weeks old female BALB/C mouse. When boost immunization with about 3-4 injections was confirmed, blood samples were drawn from the tail of the mouse to determine the antibody concentration by ELISA (enzyme-linked immunosorbent assay).

Splenocytes collected from the mouse immunized by antigen injection were cell-fused with myeloma cells to obtain 18 hybridoma cell line clones capable of continuously being subcultured and producing the antibody in an artificial culture condition.

Example 9

Western Blot Assay of KRT19 Monoclonal Antibody Produced from Hybridoma Clones

Figure 12:
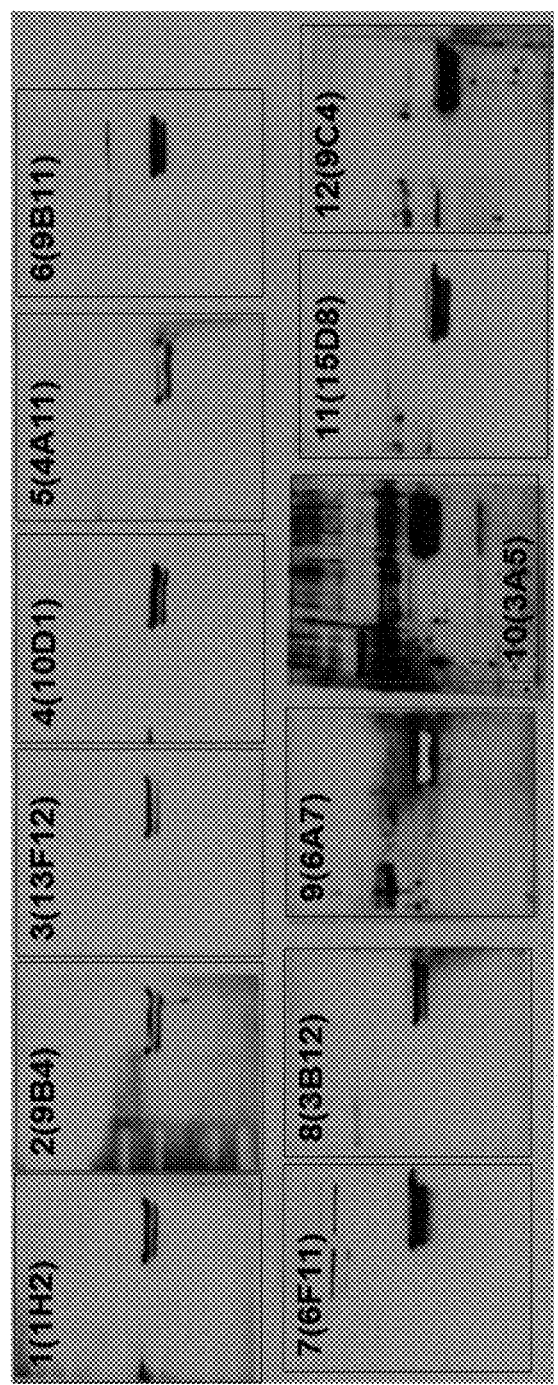
FIG. 12 is the results of Western blot analysis of 18 clones of KRT19 hybridoma.

Antibodies were obtained from 18 hybridomas of Example 8 and purified and Western blot assay was carried out to verify whether antibodies bind specifically to KRT19 (FIG. 12).

Consequently, as shown in FIG. 12, all clones showed KRT19-specific binding. The first lane is a KRT19 negative control, which uses a protein of 293T cell line; and the second lane is a KRT19 positive control, which uses MCF-7 HER2 cell line.

Example 10

Selection of Hybridoma Clone Inducing Death of HER2-Overexpressing Cells

Antibodies were obtained from 18 hybridomas prepared in Example 18 and purified and treated to HER2-overexpressing cells to select hybridoma clones inhibiting cell growth. The experimental method was carried out identically to a MTT assay in Example 7 (FIG. 13).

Figure 13:
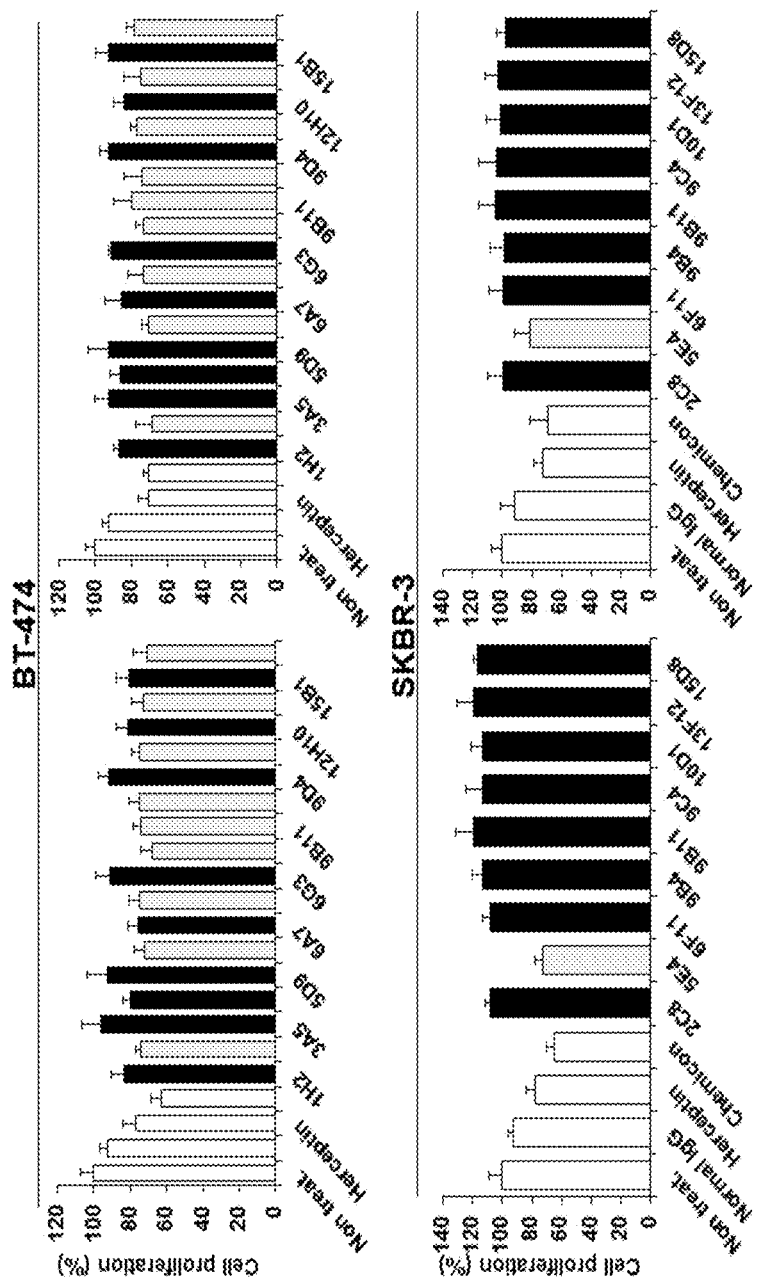
FIG. 13 is the comparative bar graph of cell proliferation for selecting KRT19 hybridoma clones.

Consequently, as shown in FIG. 13, after treatment of 18 clones to a HER2-overexpressing cell line BT-474 and selection of 9 clones having cell growth-inhibitory effect, followed by treatment of 9 clones to a HER2-overexpressing cell line SKBR-3, 5E4 clone which showed the largest cell growth-inhibitory effect was selected (FIG. 13).

Figure 14:
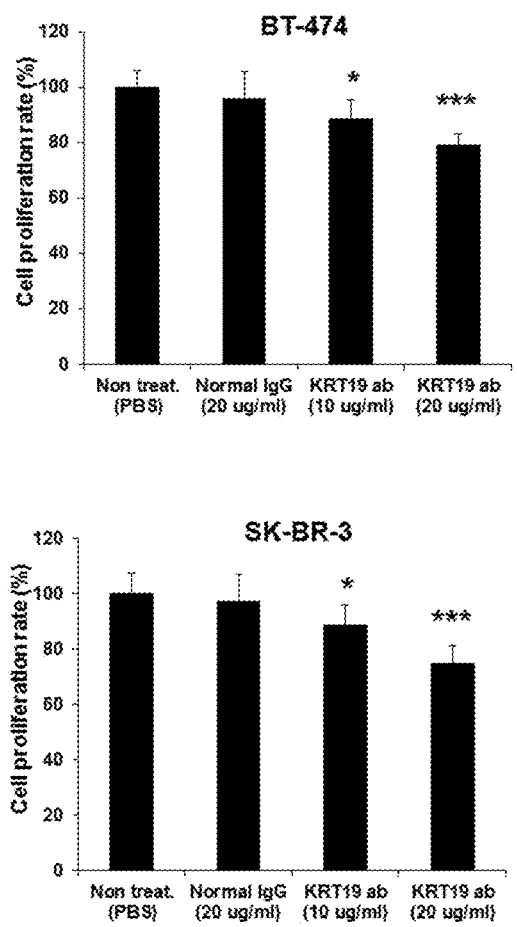
FIG. 14 is the comparative bar graph of cell proliferation for reverifying anticancer effect of selected KRT19 hybridoma 5E4.

In addition, among the above hybridoma clones, 5E4 hybridoma clone was cultured and injected to a BALB/C mouse. After 1-2 weeks, ascites fluid was obtained and purified by an antibody purification kit (Millipore), and anticancer effect was verified in a concentration-dependent manner. Consequently, as shown in FIG. 14, the inhibition of HER2-expressing cell growth was confirmed.

Although the KRT19 binding to HER2 and use thereof have been described with reference to the specific embodiments, they are not limited thereto. Therefore, it will be readily understood by those skilled in the art that various modifications and changes can be made thereto without departing from the spirit and scope of the present invention defined by the appended claims.

What is claimed is:

1. A method of decreasing the stability of HER2 (human epidermal growth factor receptor 2) in an individual having a HER2-positive cancer comprising: administering an effective amount of an expression or activity inhibitor of KRT19 (cytokeratin 19) to the individual, wherein the activity inhibitor of KRT19 is an antibody which binds specifically to KRT19 protein.

2. The method of claim 1, wherein the expression inhibitor of KRT19 is any one selected from the group consisting of antisense oligonucleotide, short interfering RNA, short hairpin RNA, and RNAi, which binds complementarily to mRNA of KRT19 gene.

3. The method of claim 1, further comprising administering a therapeutically effective amount of an expression or activity inhibitor of HER2, wherein the activity inhibitor of HER2 is an antibody which binds specifically to HER2 protein.

4. The method of claim 3, wherein the expression inhibitor of HER2 is any one selected from the group consisting of antisense oligonucleotide, short interfering RNA, short hairpin RNA, and RNAi, which binds complementarily to mRNA of HER2 gene.

5. The method of claim 3, wherein the antibody binds specifically to HER2 protein is Herceptin.

6. A method of treating a patient having a HER2-positive cancer comprising: administering a therapeutically effective amount of an expression inhibitor of KRT19 (cytokeratin 19) or an antibody which binds specifically to KRT19 to the cancer patient.

7. The method of claim 6, wherein the HER2-positive cancer is a cancer selected from the group consisting of ovarian cancer, peritoneal cancer, fallopian tubal cancer, breast cancer, non-small cell lung cancer (NSCLC), squamous cell cancer, prostate cancer and colorectal cancer.

8. The method of claim 6, wherein the expression inhibitor of KRT19 is any one selected from the group consisting of antisense oligonucleotide, short interfering RNA, short hairpin RNA, and RNAi, which binds complementarily to mRNA of KRT19 gene.

9. The method of claim 6, further comprising administering a pharmaceutically effective amount of the expression or activity inhibitor of HER2 to the patient, wherein the activity inhibitor of HER2 in an antibody which binds specifically to HER2 protein.

10. The method of claim 9, wherein the expression inhibitor of HER2 is any one selected from the group consisting of antisense oligonucleotide, short interfering RNA, short hairpin RNA, and RNAi, which binds complementarily to mRNA of HER2 gene.

11. The method of claim 9, wherein the antibody binds specifically to HER2 protein is Herceptin.

* * * * *